(12) United States Patent
Galloway et al.

(10) Patent No.: US 11,064,877 B2
(45) Date of Patent: Jul. 20, 2021

(54) LARYNGOSCOPE

(71) Applicant: INSCOPE MEDICAL SOLUTIONS, INC., Louisville, KY (US)

(72) Inventors: Margaret Galloway, Louisville, KY (US); Adam Casson, Louisville, KY (US)

(73) Assignee: Flexicare (Group) Limited, Mountain Ash (GB)

( * ) Notice: Subject to any disclaimer, the term of this patent is extended or adjusted under 35 U.S.C. 154(b) by 117 days.

(21) Appl. No.: 16/071,412

(22) PCT Filed: Mar. 1, 2017

(86) PCT No.: PCT/US2017/020242
§ 371 (c)(1),
(2) Date: Jul. 19, 2018

(87) PCT Pub. No.: WO2017/151796
PCT Pub. Date: Sep. 8, 2017

(65) Prior Publication Data
US 2020/0170498 A1 Jun. 4, 2020

Related U.S. Application Data

(60) Provisional application No. 62/301,635, filed on Mar. 1, 2016, provisional application No. 62/301,634, filed on Mar. 1, 2016.

(51) Int. Cl.
| | | |
|---|---|---|
| A61B 1/267 | (2006.01) |
| A61B 1/00 | (2006.01) |
| A61B 1/05 | (2006.01) |
| A61B 1/06 | (2006.01) |

(52) U.S. Cl.
CPC .......... *A61B 1/267* (2013.01); *A61B 1/00066* (2013.01); *A61B 1/00091* (2013.01); *A61B 1/00094* (2013.01); *A61B 1/05* (2013.01); *A61B 1/06* (2013.01)

(58) Field of Classification Search
CPC .............. A61B 1/267; A61B 1/06; A61B 1/05
See application file for complete search history.

(56) References Cited

U.S. PATENT DOCUMENTS

| | | |
|---|---|---|
| 3,848,587 A | 11/1974 | McDonald |
| 5,702,351 A | 12/1997 | Bar-Or et al. |
| 5,897,489 A | 4/1999 | Urbanowicz et al. |
| 7,608,040 B1 | 10/2009 | Dunst |
| 2001/0051766 A1 | 12/2001 | Gazdzinski |

(Continued)

FOREIGN PATENT DOCUMENTS

| | | |
|---|---|---|
| AU | 2015210829 A1 | 8/2016 |
| CA | 2937890 A1 | 8/2015 |

(Continued)

OTHER PUBLICATIONS

International Preliminary Report on Patentability for PCT/US2017/020242 dated Sep. 4, 2018.

(Continued)

*Primary Examiner* — Andrew Yang
(74) *Attorney, Agent, or Firm* — Nixon Peabody LLP

(57) ABSTRACT

Improved laryngoscopes are disclosed herein which are capable of aiding operators toward successful intubation outcomes in clinical situations which would be difficult using previously existing tools.

62 Claims, 19 Drawing Sheets

(56) References Cited

U.S. PATENT DOCUMENTS

| | | |
|---|---|---|
| 2002/0022769 A1 | 2/2002 | Smith et al. |
| 2002/0082475 A1 | 6/2002 | Stahl et al. |
| 2007/0287888 A1 | 12/2007 | Lovell et al. |
| 2010/0121152 A1 | 5/2010 | Boedeker |
| 2010/0256482 A1 | 10/2010 | Peters et al. |
| 2010/0261968 A1 | 10/2010 | Nearman et al. |
| 2011/0028790 A1 | 2/2011 | Farr et al. |
| 2011/0092773 A1 | 4/2011 | Goldstein |
| 2011/0130627 A1 | 6/2011 | McGrail et al. |
| 2011/0178372 A1 | 7/2011 | Pacey et al. |
| 2012/0035502 A1 | 2/2012 | Menegazzi |
| 2013/0060090 A1 | 3/2013 | McGrath et al. |
| 2013/0104884 A1 | 5/2013 | Vazales et al. |
| 2013/0197312 A1 | 8/2013 | Miller et al. |
| 2016/0000300 A1 | 1/2016 | Williams |
| 2016/0345803 A1 | 12/2016 | Mallory et al. |
| 2018/0214013 A1 | 8/2018 | Casson |

FOREIGN PATENT DOCUMENTS

| | | |
|---|---|---|
| CA | 3015226 A1 | 9/2017 |
| CN | 1452472 A | 10/2003 |
| CN | 102481086 A | 5/2012 |
| CN | 106132281 A | 11/2016 |
| CN | 108697318 A | 10/2018 |
| EP | 1 977 685 A1 | 10/2008 |
| EP | 3099216 A1 | 12/2016 |
| EP | 3331420 | 6/2018 |
| EP | 3422925 A1 | 1/2019 |
| JP | 2017504465 A | 2/2017 |
| MX | 2016009802 A | 1/2017 |
| TH | 177022 | 6/2018 |
| WO | WO 2007/070943 A1 | 6/2007 |
| WO | 2012172076 A1 | 12/2012 |
| WO | 2014105649 A1 | 7/2014 |
| WO | 2015116900 A1 | 8/2015 |
| WO | 2017024007 A1 | 2/2017 |
| WO | 2017151796 A1 | 9/2017 |

OTHER PUBLICATIONS

Extended European Search Report for EP 17 76 0734 dated Oct. 2, 2019 (8 pages).
International Search Report and Written Opinion for PCT/US2015/013690 dated May 6, 2015, 8 pages.
International Preliminary Report on Patentability for PCT/US2015/013690 dated Aug. 2, 2016, 7 pages.
International Search Report and Written Opinion for PCT/US2016/045299 dated Oct. 26, 2016, 13 pages.
International Preliminary Report on Patentability for PCT/US2016/045299 dated Feb. 6, 2018, 11 pages.
International Search Report and Written Opinion for PCT/US2017/020242 dated May 15, 2017, 22 pages.
EP Extended Search Report for 15743864.9 dated Aug. 30, 2017, 6 pages.
EP Examination Report for EP 15743864.9 dated Jan. 22, 2019, 3 pages.

LARYNGOSCOPE

CROSS-REFERENCE TO RELATED APPLICATIONS

This application is a National Phase of International Application No. PCT/US2017/020242, filed Mar. 1, 2017, currently pending, which designated the U.S. and that International Application was published under PCT Article 21(2) in English, which also includes a claim of priority under 35 U.S.C. § 119(e) to U.S. provisional patent application Nos. 62/301,634, filed Mar. 1, 2016, and 62/301,635, filed Mar. 1, 2016, the entirety of which is hereby incorporated by reference.

BACKGROUND

In the field of emergency medicine, the process of intubation is often stymied by the presence of excess fluid such as blood or mucus as well as anatomical features that are either the result of injuries or a patients' body habitus. To that end, improved laryngoscopes are disclosed herein which are capable of aiding operators toward successful intubation outcomes in clinical situations which would be difficult using previously existing tools.

SUMMARY OF THE DISCLOSURE

According to certain embodiments of the present disclosure, a laryngoscope is disclosed having a distinct blade portion and handle portion, wherein the blade portion includes at least one inlet, wherein the handle portion includes at least one outlet, wherein the at least one internal passageway formed within the blade portion for fluid communication with the at least one inlet and the at least one outlet and is further configured to extend through at least a portion of the cross-section of the handle, wherein the handle portion is sized and shaped to be optionally coupled to a removable electronic component module, and wherein the removable electronic component module provides at least one functionality of pH sensing, $CO_2$ sensing, acoustic sensing, capacitance sensing, inductance sensing, temperature sensing, specific molecule sensing, binocular image sensing, monocular image sensing, arrayed image sensing, ambient color sensing, or generating light and measuring the frequency of light that is reflected by the surroundings.

According to certain embodiments of the present disclosure, a laryngoscope is disclosed having a distinct blade portion and handle portion, wherein the blade portion includes at least one inlet, wherein the handle portion includes at least one outlet, wherein the at least one internal passageway formed within the blade portion for fluid communication with the at least one inlet and the at least one outlet and is further configured to extend through at least a portion of the cross-section of the handle, wherein the handle portion is sized and shaped to be optionally coupled to an electronic component module, and wherein the electronic component module provides at least one functionality of pH sensing, $CO_2$ sensing, acoustic sensing, capacitance sensing, inductance sensing, temperature sensing, specific molecule sensing, binocular image sensing, monocular image sensing, arrayed image sensing, ambient color sensing, or generating light and measuring the frequency of light that is reflected by the surroundings.

The laryngoscope may further include at least one sensor that is configured to detect static states or changes in state of the following airway characteristics: pH, CO2, acoustic feedback, fluid and/or tissue capacitance, fluid and/or tissue inductance, ambient temperature, specific molecule(s), binocular image data, monocular image data, arrayed image data, or ambient color, the sensor data to be sent to the electronic component module for processing. The sensor may also generate light and measure frequency of light.

According to further embodiments of the present disclosure, the electronic component module may include at least one of onboard circuitry for amplifying the output of the at least one sensor, onboard circuitry for conditioning the output of the at least one sensor, onboard circuitry for converting the output of the at least one sensor into a machine-readable format, onboard circuitry for transmitting the output of the at least one sensor to a remote device distinct from the laryngoscope via a physical wire, onboard circuitry for transmitting the output of the at least one sensor to a remote device distinct from the laryngoscope via radio, onboard circuitry for transmitting the output of the at least one sensor to a remote device distinct from the laryngoscope via Bluetooth, onboard circuitry for transmitting the output of the at least one sensor to a remote device distinct from the laryngoscope via WIFI.

According to further embodiments of the present disclosure, the electronic component module may include at least one integrated wireless communication radio providing at least one functionality of 2.4 ghz Wi-Fi frequency, 5.0 ghz Wi-Fi frequency, Bluetooth, analogue data radio, 3g mobile data network, 4g mobile data network, 4g LTE mobile data network, and 5g mobile data network connectivity.

According to further embodiments of the present disclosure, the electronic component module may include at least one data processing unit that is configured to provide at least one functionality of hardware video encoding, general data processing, firmware storage and management, data encryption, audio encoding, visible and invisible spectrum light analysis, current analysis, or image depth processing.

According to further embodiments of the present disclosure, the data processing units may utilize at least one architecture of Reduced Instruction Set Computer (RISC), Microprocessor without Interlocked Pipeline Stages (MIPS), Advanced RISC Machine (ARM), ARM 32 bit (AArch32), ARM 64 bit (AArch64), Single instruction multiple data (SIMD), Single instruction multiple threads (SIMT), Multiple instruction streams multiple data streams (MIMD), x86, or x86 Atom.

According to further embodiments of the present disclosure, the at least one data processing unit may encode video data to at least one codec standard of MJPEG, H.264, HEVC, H.265, MPEG-4, or MJPEG.

According to further embodiments of the present disclosure, raw video data from the at least one sensor may be encoded using an integrated hardware encoder.

According to further embodiments of the present disclosure, the electronic component module may include an onboard battery for the power consumption needs of its sensor(s) and associated components.

According to further embodiments of the present disclosure, the electronic component module may include a distinct conductor for receiving power from a device distinct from the laryngoscope.

According to further embodiments of the present disclosure, the electronic component module may be configured to draw current from an LED or Lighting conductor(s) which are present in the laryngoscope, where the LED or Lighting functionality of the laryngoscope is independent of the presence of the electronic component module.

According to further embodiments of the present disclosure, the electronic component module may include a body sized and shaped to be coupled to the cephalic portion of the laryngoscope handle.

According to further embodiments of the present disclosure, the electronic component module may be sized and shaped to be coupled to the proximal face of the handle.

According to further embodiments of the present disclosure, the electronic component module may be sized and shaped to be coupled to the "heel" of the laryngoscope, wherein the "heel" is the portion near the junction between the handle and the blade portion.

According to further embodiments of the present disclosure, the electronic component module may be coupled to the laryngoscope via a door disposed upon the handle of the laryngoscope, thereby exposing a cavity therein.

According to further embodiments of the present disclosure, the coupling of the door to the handle may be selected from one of, a removable door, a sliding door, a mechanically hinged door, or a live hinged door.

According to further embodiments of the present disclosure, the laryngoscope may include a movable "entry" face disposed upon the surface of the handle, such that when the electronic component module is urged against the entry face, the entry face and electronic component module are translated into the handle until the electronic component module is coupled to a complementary engagement mechanism disposed within the handle, thereby mechanically coupling the electronic component module to the handle.

According to further embodiments of the present disclosure, the laryngoscope may include a tube having a sensor at its end, with the tube extending from the caudal end portion of the electronic component module, such that when the electronic component module is coupled to the laryngoscope, the tube extends through a cavity in the laryngoscope and a substantial portion of the blade portion, thereby orienting the end of the tube near one of a window or aperture disposed upon the blade portion.

In another embodiment of the present disclosure, the sensing functionality may already be present in the laryngoscope and become enabled by the presence of the electronic component module, including for instance if a camera or inductance sensor is built into the blade portion and only capable of transmitting its information in the presence of the electronic component module.

According to further embodiments of the present disclosure, the laryngoscope may include an optional suction inlet near the tip of the blade portion, wherein the suction is automatically engaged or disengaged depending on the state of one of the at least one sensor inputs including for instance a capacitance, temperature, or image readout indicative of the presence of unwanted fluid.

According to further embodiments of the present disclosure, the blade portion may be hinged and thereby capable of being configured as either a traditional or high angle laryngoscope.

According to further embodiments of the present disclosure, the hinging action may be modulated by the presence or absence of the electronic component module.

According to further embodiments of the present disclosure, the specific molecule sensing functionality may be achieved using a Microelectromechanical systems (MEMS) configured to recognize at least one of $O_2$, $N_2$, $CO_2$, HCl, NaCl, and KCl.

According to further embodiments of the present disclosure, the MEMS may be selected from one of a contact sensor or a sensor for measuring present ambient gasses.

According to certain embodiments of the present disclosure, a laryngoscope includes: a laryngoscope having a distinct blade portion and handle portion, with a fluid channel extending through at least a portion of the cross-section of the handle; with the handle portion being sized and shaped to be coupled to a removable electronic component module, wherein the electronic component module is configured to collect and analyze at least one of the following output: pH sensing, $CO_2$ sensing, acoustic sensing, capacitance sensing, inductance sensing, temperature sensing, specific molecule sensing, binocular image sensing, monocular image sensing, arrayed image sensing, ambient color sensing, or generating light and measuring the frequency of light that is reflected by the surroundings; wherein the electronic component module is configured to send the output to a remote device, and wherein the remote device includes a user interface selected from one of acoustic feedback, haptic feedback, and visual feedback that communicates secondary information derived from the output of the electronic component module to operator of the laryngoscope.

According to further embodiments of the present disclosure, the visual feedback may be provided by one of at least one selectively illuminated LED, a nonreflective e-ink style display, or a reflective LCD style display.

According to further embodiments of the present disclosure, the LED or display may be disposed upon the body of the device.

According to further embodiments of the present disclosure, the LED or display may be disposed within a body distinct from the laryngoscope.

According to further embodiments of the present disclosure, the body distinct from the laryngoscope may include the electronic component module wherein the LED, LED array, or display remains distinct from the laryngoscope until the module is connected to or inserted into the laryngoscope body.

According to further embodiments of the present disclosure, the secondary information may be selected from at least one of: position relative to anatomical landmarks, likelihood of relative position, or presence of a predetermined sensor state.

According to further embodiments of the present disclosure, the electronic component module may be configured to identify anatomic markers based on their visual appearance including at least one of: molars, soft palate, palatoglossal arch, uvula, palatine tonsil, palatopharyngeal arch, oropharynx, epiglottis, esophagus, glottis, cuneiform tubercle, corniculate tubercle, true vocal chords, false vocal chords, open vocal chords, or closed vocal chords.

According to further embodiments of the present disclosure, the electronic component module may be configured to integrate the readouts of multiple sensors to improve the certainty that the blade portion is in a given anatomical position including for instance the sound of the trachea, lower pH of the esophagus, or UV reflectivity of the vocal chords.

According to further embodiments of the present disclosure, the specific molecule sensing functionality may be achieved using a MEMS configured to recognize at least one of $O_2$, $N_2$, $CO_2$, HCl, NaCl, and KCl.

According to further embodiments of the present disclosure, the MEMS may be selected from one of a contact sensor or a sensor for measuring present ambient gasses.

According to further embodiments of the present disclosure, the visual feedback may be provided as an overlay atop a live image from a camera near the tip of the blade portion.

According to further embodiments of the present disclosure, the visual feedback may be provided by providing a live wireframe style outline of the relevant anatomical features and path which the operator should follow.

According to further embodiments of the present disclosure, the electronic component module may be configured to provide feedback regarding location derived from sensor state either upon prompting by the operator or automatically upon recognizing a distinct location or sensor state.

According to further embodiments of the present disclosure, the electronic component module may be configured to provide feedback to guide the operator to a path of successful intubation.

According to further embodiments of the present disclosure, the electronic component module may be configured to provide said feedback to verify previous steps already taken by the operator.

According to further embodiments of the present disclosure, the electronic component module may be configured to record both raw data from the at least one sensor and integrated assumptions about position to document the course of the procedure.

According to further embodiments of the present disclosure, the recording occurs upon a device distinct from the laryngoscope but in electronic communication therewith including for instance a network attached or cloud storage server.

According to further embodiments of the present disclosure, the radio may be configured to perform a test to find the least utilized frequency channel within a 50 ft radius about the device upon boot up and selects the least utilized frequency channel for streaming data from the at least one sensor.

According to further embodiments of the present disclosure, the radio may be configured to perform a utilization test of channels 1, 6, and 11 within the 2.4 ghz frequency and selects the least utilized or defaults to channel 11 for streaming data from the at least one sensor, if less than 2.5% utilization difference found.

According to further embodiments of the present disclosure, the radio may be configured to perform a utilization test of all channels within the 5.0 ghz frequency and selects the least utilized or defaults to a preset channel if less than 2.5% utilization difference found for streaming data from the at least one sensor.

According to further embodiments of the present disclosure, the wireless radio performs a utilization test of all channels within the 2.4 ghz frequency and selects the least utilized or defaults to channel 11 for streaming data from the at least one sensor, if less than 2.5% utilization difference found.

According to further embodiments of the present disclosure, the electronic sensor module may use a Linux Embedded Development Environment (LEDE) to manage the at least one of onboard circuitry.

According to further embodiments of the present disclosure, the electronic sensor module may use at least one of streamer or UDP over RTP to stream video data to the user interface.

According to further embodiments of the present disclosure, the video data stream may be encrypted via a symmetric encryption protocol, including Advanced Encryption Standard (AES) 128 bit, 192 bit, or 256 bit.

According to further embodiments of the present disclosure, a proximal face of intersection of the handle and the blade portion may form a curve with a radius of not more than 2.15 in and not less than 1.40 in.

According to further embodiments of the present disclosure, a distal face of intersection of the handle and the blade portion may form a curve with a radius of not more than 0.85 in and not less than 0.25 in.

According to further embodiments of the present disclosure, the proximal face of the handle features a change in depth of not more than 10 mm and not less than 2 mm.

According to further embodiments of the present disclosure, the distal face of the handle features a change in depth of not more than 18 mm and not less than 8 mm.

According to further embodiments of the present disclosure, the handle may include a valve button wherein the valve button is located no more than 4.20 inches and not less than 3.75 inches from the base of the handle.

According to further embodiments of the present disclosure, the user interface is a tablet or smartphone application that automatically detects high ambient light conditions with the forward-facing camera or light sensor and adjusts at least one of screen brightness, image contrast, or image coloration.

According to further embodiments of the present disclosure, the user interface is a tablet or smartphone application that uses an algorithm to generate a unique password for the SSID of each laryngoscope.

According to further embodiments of the present disclosure, the at least one data processor uses a computer vision algorithm to analyze the sensor data stream to provide the user with secondary guidance information.

According to further embodiments of the present disclosure, the at least one data processor uses a computer vision algorithm to analyze the MJPEG video stream to provide the user with more secondary guidance information due to the increased number of key frames relative to other video codecs.

SELECTED EMBODIMENTS

Embodiment 1

A laryngoscope comprising; a handle comprising a top portion, a bottom portion, and at least one outlet; a blade with a distal tip and a proximal portion wherein the proximal portion is connected to the bottom portion of the handle; at least one fluid channel that is configured to extend through at least a portion of cross-section of the handle and the blade; at least one sensor that is located between the proximal portion and the distal tip of the blade and further configured to detect raw data once intubated in a patient; an electronic component module, wherein the blade is configured to protrude outwardly at a substantially perpendicular angle from the handle to the distal tip, wherein the blade further comprises: (a) at least one inlet near the distal tip; and (b) at least one inlet between the distal tip and the proximal tip, wherein the handle is sized and shaped to be coupled to the electronic component module, wherein the electronic component module comprises integrated circuitry which provides at least one functionality of: pH sensing, $CO_2$ sensing, acoustic sensing, capacitance sensing, inductance sensing, temperature sensing, specific molecule sensing, binocular image sensing, monocular image sensing, arrayed image sensing, ambient color sensing, USB video device class (UVC), generating light and measuring the frequency of light that is reflected by its surroundings, or any combination thereof, and wherein the at least one outlet, the at least one inlet near the distal tip, the at least one inlet between the distal tip and the proximal tip, and the at least one fluid channel, are configured to be in fluid communication with each other.

Embodiment 2

The laryngoscope of embodiment 1, wherein the raw data comprises at least one of: video file, pH level, $CO_2$ level, temperature, specific molecule, sound of trachea, lower pH of esophagus, UV reflectivity of vocal chords, or any combination thereof.

Embodiment 3

The laryngoscope of embodiment 1, further comprising at least one valve that is located within the handle and configured to control the fluid communication between the at least one inlet, the at least one outlet, and the at least one suction channel.

Embodiment 4

The laryngoscope of embodiment 1, further comprising a sensor cavity within the handle and the blade that is configured to extend from the electronic component module to the at least one sensor.

Embodiment 5

The laryngoscope of embodiment 3, further comprising a flexible sensor tube that is configured to connect the electronic component module to the at least one sensor in order to transmit data from the at least one sensor to the electronic component module.

Embodiment 6

The laryngoscope of embodiment 1, wherein the raw data detected by the at least one sensor comprises at least one of: pH, $CO_2$, acoustic, capacitance, inductance, temperature, specific molecule, binocular image, monocular image, arrayed image, ambient color, or any combination thereof.

Embodiment 7

The laryngoscope of embodiment 1, wherein the electronic component module further comprises: (a) a battery that provides power to the electronic component module and the at least one sensor through the sensor tube; (b) a sensory data encoder that encodes the raw data that it receives from the at least one sensor and transmit the encoded data to a data processing unit; (c) the data processing unit that processes encoded data; and (d) a network radio that is configured to receive the processed data from the data processing unit and transmit the processed data to an external source.

Embodiment 8

The laryngoscope of embodiment 7, wherein the external source comprises at least one of: a remote device, a system computer, a server, a database, or any combination thereof.

Embodiment 9

The laryngoscope of embodiment 7, wherein the network radio is configured to receive instructions from a user with regards to use of the laryngoscope.

Embodiment 10

The laryngoscope of embodiment 9, wherein the instructions comprise at least one of the following: begin collecting the fluid, stop collecting the fluid, slow down the fluid communication, transmit the data, turn on the power on the electronic component module, turn off the power on the electronic component module, or any combination thereof.

Embodiment 11

The laryngoscope of embodiment 1, wherein the handle further comprises contacts.

Embodiment 12

The laryngoscope of embodiment 11, wherein the blade further comprises an inductive sensing module near the at least one inlet.

Embodiment 13

The laryngoscope of embodiment 12, wherein the inductive sensing module comprises at least one of electrical leads, inductive coil, or any combination thereof.

Embodiment 14

The laryngoscope of embodiment 13, wherein the contacts and the inductive sensing module are configured to establish electrical communication when the electronic component module is attached to the handle.

Embodiment 15

The laryngoscope of embodiment 1, wherein the electronic component module is configured to be removable from the handle.

Embodiment 16

The laryngoscope of embodiment 1, wherein the at least one inlet between the distal tip and the proximal tip is located in close proximity to the at least one sensor.

Embodiment 17

The laryngoscope of embodiment 16, wherein the at least one inlet between the distal tip and the proximal tip is configured to exert air in order to clean the at least one sensor.

Embodiment 18

The laryngoscope of embodiment 16, wherein the at least one inlet between the distal tip and the proximal tip is configured to exert fluid that circulates in the laryngoscope via the at least one fluid channel in order to clean the at least one sensor.

Embodiment 19

The laryngoscope of embodiment 1, wherein the integrated circuitry contains at least one integrated wireless communication radio.

Embodiment 20

The laryngoscope of embodiment 19, wherein the at least one integrated wireless communication radio is configured to provide at least one functionality of 2.4 ghz wifi frequency, 5.0 ghz wifi frequency, Bluetooth, analogue data radio, 3g mobile data network, 4g mobile data network, 4g LTE mobile data network, and 5g mobile data network connectivity.

Embodiment 21

The laryngoscope of embodiment 19, wherein the integrated circuitry comprises at least one of: onboard circuitry for amplifying output of the at least one sensor, onboard circuitry for conditioning the output of the at least one sensor, onboard circuitry for converting the output of the at least one sensor into a machine-readable format, onboard circuitry for transmitting the output of the at least one sensor to a remote device distinct from the laryngoscope via a physical wire, onboard circuitry for transmitting the output of the at least one sensor to a remote device distinct from the laryngoscope via the at least one integrated wireless communication radio, onboard circuitry for transmitting the output of the sensor to a remote device distinct from the laryngoscope via communications network, or any combination thereof.

Embodiment 22

The laryngoscope of embodiment 2, wherein the electronic component module provides at least one data processing unit that is configured to provide at least one functionality of: hardware video encoding, general data processing, firmware storage and management, data encryption, audio encoding, visible and invisible spectrum light analysis, current analysis, image depth processing, or any combination thereof.

Embodiment 23

The laryngoscope of embodiment 22, wherein at least one of the data processing units utilizes at least one architecture of: Reduced Instruction Set Computer (RISC), Microprocessor without Interlocked Pipeline Stages (MIPS), Advanced RISC Machine (ARM), ARM 32 bit (AArch32), ARM 64 bit (AArch64), Single instruction multiple data (SIMD), Single instruction multiple threads (SIMT), Multiple instruction streams multiple data streams (MIMD), x86, or x86 Atom, or any combination thereof.

Embodiment 24

The laryngoscope of embodiment 23, wherein the at least one data processing unit encodes the raw data to at least one codec standard of: MJPEG, H.264, HEVC, H.265, or MPEG-4, or any combination thereof.

Embodiment 25

The laryngoscope of embodiment 22, wherein the raw data is encoded using an integrated hardware encoder.

Embodiment 26

The laryngoscope of embodiment 1, wherein the integrated circuitry comprises an onboard battery for power consumption needs of the at least one sensor.

Embodiment 27

The laryngoscope of embodiment 1, wherein the electronic component module includes a distinct conductor for receiving power from a device distinct from the laryngoscope.

Embodiment 28

The laryngoscope of embodiment 1, further comprising at least one of: LED, lighting conductor, or any combination thereof.

Embodiment 29

The laryngoscope of embodiment 1, wherein the LED functions independent of the electronic component module.

Embodiment 30

The laryngoscope of embodiment 28, wherein the electronic component module is configured to draw current from at least one of: the LED, the lighting conductor, or any combination thereof.

Embodiment 31

The laryngoscope of embodiment 1, wherein the electronic component module is configured to be sized and shaped to be coupled to the laryngoscope handle.

Embodiment 32

The laryngoscope of embodiment 1, wherein the electronic component module is sized and shaped to be coupled to the bottom of the handle.

Embodiment 33

The laryngoscope of embodiment 1, wherein the electronic component module is configured to be coupled to the laryngoscope via a door disposed upon the handle, thereby exposing a cavity therein.

Embodiment 34

The laryngoscope of embodiment 33, wherein the coupling of the door to the handle is selected from one of, a removable door, a sliding door, a mechanically hinged door, or a live hinged door.

Embodiment 35

The laryngoscope of embodiment 1, wherein the handle comprises a movable entry face on outer surface of the handle, such that when the electronic component module is urged against the entry face, the entry face and electronic component module are translated into the handle until the electronic component module is coupled to a complementary engagement mechanism disposed within the handle, thereby mechanically coupling the electronic component module to the handle.

Embodiment 36

The laryngoscope of embodiment 1, wherein the blade is hinged and thereby capable of being configured as either a traditional or high-angle laryngoscope.

Embodiment 37

The laryngoscope of embodiment 36, wherein the hinging is modulated by the presence of the electronic component module.

Embodiment 38

The laryngoscope of embodiment 36, wherein the hinging is modulated by the absence of the electronic component module.

Embodiment 39

The laryngoscope of embodiment 36, wherein the hinging is modulated upon detection of excess fluid by the at least one sensor.

Embodiment 40

The laryngoscope of embodiment 36, wherein the hinging is modulated upon detection of abnormal anatomy inside the patient by the at least one sensor.

Embodiment 41

The laryngoscope of embodiment 1, wherein the specific molecule sensing functionality is achieved using the at least one sensor that is configured to recognize at least one of $O_2$, $N_2$, CO2, HCl, NaCl, and KCl.

Embodiment 42

The laryngoscope of embodiment 41, wherein the at least one sensor comprises at least one of: a contact sensor, a sensor for measuring present ambient gasses, or any combination thereof.

Embodiment 43

The laryngoscope of embodiment 1, wherein the at least one inlet between the distal tip and the proximal tip is oriented so as to clear the at least one sensor when the at least one sensor is obscured by fluid or tissue by applying a vacuum to the at least one outlet.

Embodiment 44

The laryngoscope of embodiment 2, wherein the electronic component module is capable of creating a visual feedback that identifies at least one anatomic marker inside the patient based on the raw data detected by the at least one sensor.

Embodiment 45

The laryngoscope of embodiment 44, wherein the anatomic marker comprises at least one of: molars, soft palate, palatoglossal arch, uvula, palatine tonsil, palatopharyngeal arch, oropharynx, epiglottis, esophagus, glottis, cuneiform tubercle, conciculate tubercle, true vocal chords, false vocal chords, open vocal chords, closed vocal chords, or any combination thereof.

Embodiment 46

The laryngoscope of embodiment 44, wherein the electronic component module is capable of integrating the raw data from more than one of the at least one sensor to improve the certainty that the blade is in a given anatomical marker inside the patient.

Embodiment 47

The laryngoscope of embodiment 44, further comprising at least one of the following visual display to display the visual feedback: illuminated LED, a selectively illuminated LED array, a non-reflective e-ink style display, or a reflective LCD style display.

Embodiment 48

The laryngoscope of embodiment 44, wherein the electronic component module is configured to transmit the visual feedback to at least one of: a remote device, a server, a database, a system computer, or any combination thereof.

Embodiment 49

The laryngoscope of embodiment 48, wherein the visual feedback is provided as an overlay atop a live image from a camera near the tip of the blade.

Embodiment 50

The laryngoscope of embodiment 49, wherein the visual feedback is provided by providing a live wireframe style outline of anatomical features and path which the blade should follow inside the patient.

Embodiment 51

The laryngoscope of embodiment 44, wherein the visual feedback is displayed in a user interface to assist a user to guide the laryngoscope inside the patient for a path to successful intubation.

Embodiment 52

The laryngoscope of embodiment 1, wherein the electronic sensor module uses a Linux Embedded Development Environment (LEDE) to manage the integrated circuitry.

Embodiment 53

A system for intubation of a laryngoscope comprising: a laryngoscope that measures and transmits at least one output signal; a computing device configured to receive the at least one output signal from the laryngoscope and display the at least one output signal in real-time; and a graphical user interface on the computing device that allows a user to view and customize options for monitoring the at least one output signal, wherein the laryngoscope and the computing device are communicatively connected to each other via a communications network.

Embodiment 54

The system of embodiment 53, wherein the laryngoscope comprises: a handle comprising a top portion, a bottom portion, and at least one outlet; a blade with a distal tip and a proximal portion wherein the proximal portion is connected to the bottom portion of the handle; at least one suction channel that is configured to extend through at least a portion of cross-section of the handle and the blade; at least one sensor that is located between the proximal portion and the distal tip of the blade and further configured to detect raw data once intubated in a patient; an electronic component module that is configured to convert the raw data into the at least one output, wherein the blade is configured to protrude outwardly at a substantially perpendicular angle from the handle to the distal tip, wherein the blade further comprises: (a) at least one inlet near the distal tip; and (b) at least one inlet between the distal tip and the proximal tip, wherein the handle is sized and shaped to be coupled to the electronic component module, wherein the electronic component module comprises integrated circuitry, and wherein the at least one outlet, the at least one inlet near the distal tip, the at least one inlet between the distal tip and the proximal tip, and the at least one fluid channel, are configured to be in fluid communication with each other.

Embodiment 55

The system of embodiment 53, wherein the system further comprises a hosted server that is (i) configured to store and analyze the at least one output signal and (ii) connected to the local device and the computing device via the communications network.

Embodiment 56

The system of embodiment 55, wherein the hosted server is further configured to (i) determine current anatomical location of the laryngoscope inside a patient; (ii) determine a route to the preferred anatomical location inside the patient; and (iii) provide a digital guidance for a user to follow so that the user can guide the laryngoscope to the preferred anatomical location.

Embodiment 57

The system of embodiment 55, wherein the current anatomical location, the preferred anatomical location, the route to the preferred anatomical location, and the digital guidance are determined by at least one of: probability algorithm, machine learning algorithm, or combination thereof.

Embodiment 58

The system of embodiment 57, wherein probability algorithm or machine learning algorithm are stored inside the computing device.

Embodiment 59

The system of embodiment 57, wherein probability algorithm or machine learning algorithm are stored inside the laryngoscope.

Embodiment 60

The system of embodiment 54, wherein the integrated circuitry provides at least one functionality of: pH sensing, $CO_2$ sensing, acoustic sensing, capacitance sensing, inductance sensing, temperature sensing, specific molecule sensing, binocular image sensing, monocular image sensing, arrayed image sensing, ambient color sensing, USB video device class (UVC), generating light and measuring the frequency of light that is reflected by its surroundings, or any combination thereof.

Embodiment 61

A laryngoscope comprising; a handle comprising a top portion, a bottom portion, and at least one outlet; a blade with a distal tip and a proximal portion wherein the proximal portion is connected to the bottom portion of the handle; at least one fluid channel that is configured to extend through at least a portion of cross-section of the handle and the blade; at least one sensor that is located between the proximal portion and the distal tip of the blade and further configured to detect raw data once intubated in a patient; an electronic component module, wherein the blade is configured to protrude outwardly at a substantially perpendicular angle from the handle to the distal tip, wherein the blade further comprises: (a) at least one inlet near the distal tip; and (b) at least one inlet between the distal tip and the proximal tip, wherein the handle is sized and shaped to be coupled to the electronic component module, wherein the electronic component module comprises at least one integrated circuitry, and wherein the at least one outlet, the at least one inlet near the distal tip, the at least one inlet between the distal tip and the proximal tip, and the at least one fluid channel, are configured to be in fluid communication with each other.

Embodiment 62

The laryngoscope of embodiment 61, wherein the at least one integrated circuitry provides at least one functionality of: pH sensing, $CO_2$ sensing, acoustic sensing, capacitance sensing, inductance sensing, temperature sensing, specific molecule sensing, binocular image sensing, monocular image sensing, arrayed image sensing, ambient color sensing, USB video device class (UVC), generating light and measuring the frequency of light that is reflected by its surroundings, or any combination thereof.

Embodiment 63

A computer readable storage medium tangibly embodying a computer readable program code having computer readable instructions which, when implemented, cause a computer to carry out the steps of: detecting at least one anatomical feature of a patient by at least one sensor on a laryngoscope once the laryngoscope is intubated into the patient by a user; transmitting the at least one anatomical feature to an electronic component module; determining a preferred route of the laryngoscope inside the patient by the electronic component module; sending the preferred route to a remote device to be displayed as an anatomical overlay on a graphic user interface; and providing the laryngoscope to the preferred route inside the patient via the anatomical overlay.

Embodiment 64

The method of embodiment 63, wherein the at least one anatomical feature comprises at least one of: pH, $CO_2$, acoustic, capacitance, inductance, temperature, specific molecule, binocular image, monocular image, arrayed image, ambient color, or the like.

BRIEF DESCRIPTION OF THE FIGURES

In the figures, which are not necessarily drawn to scale, like numerals describe substantially similar components throughout the several views. The drawings illustrate generally, by way of example, but not by way of limitation, various embodiments discussed in the claims of the present document.

DETAILED DESCRIPTION OF THE DISCLOSURE

Figure 1A:
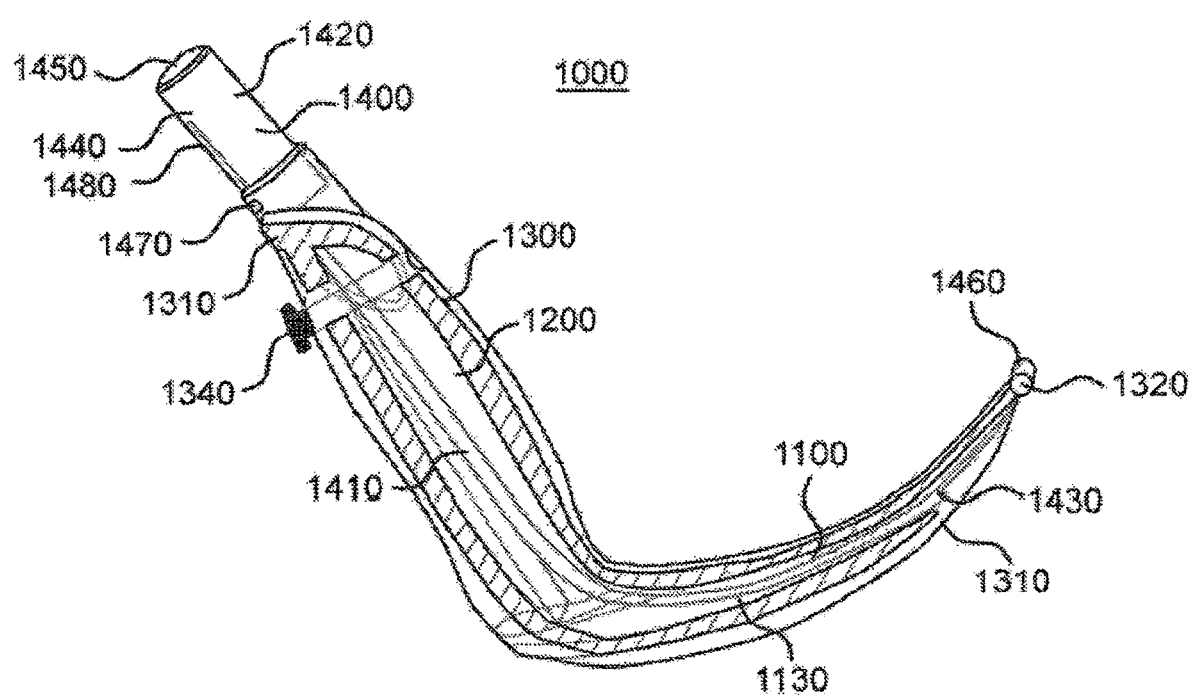
FIG. 1A shows a side perspective view of an example of an improved laryngoscope that is constructed in accordance with the principles of the present disclosure.

The disclosure and the various features and advantageous details thereof are explained more fully with reference to the non-limiting implementations and examples that are described and/or illustrated in the accompanying drawings, and detailed in the following description. It should be noted that the features illustrated in the drawings are not necessarily drawn to scale, and features of one implementation may be employed with other implementations, as any person skilled in the art would recognize, even if not explicitly stated herein. Descriptions of well-known components and processing techniques may be omitted so as to not unnecessarily obscure the implementations of the disclosure. The examples used herein are intended merely to facilitate an understanding of ways in which the disclosure may be practiced and to further enable those of skill in the art to practice the implementations of the disclosure. Accordingly, the examples and implementations herein should not be construed as limiting the scope of the disclosure.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one implementation," as used herein does not necessarily refer to the same implementation.

The term "coupled" means at least either a direct electrical connection between the connected items or an indirect connection through one or more passive or active intermediary devices. The term "circuit" means at least either a single component or a multiplicity of components, either active and/or passive, that are coupled together to provide a desired function. The term "signal" as used herein may include any meanings as may be understood by those of ordinary skill in the art, including at least an electric or magnetic representation of current, voltage, charge, temperature, data or a state of one or more memory locations as expressed on one or more transmission mediums, and generally capable of being transmitted, received, stored, compared, combined or otherwise manipulated in any equivalent manner.

Terms such as "providing," "processing," "supplying," "determining," "calculating" or the like may refer at least to an action of a computer system, computer program, signal processor, logic or alternative analog or digital electronic device that may be transformative of signals represented as physical quantities, whether automatically or manually initiated.

A "computer," as used in this disclosure, means any machine, device, circuit, component, or module, or any system of machines, devices, circuits, components, modules, or the like, which are capable of manipulating data according to one or more instructions, such as, for example, without limitation, a processor, a microprocessor, a central processing unit, a general purpose computer, a cloud, a super computer, a personal computer, a laptop computer, a palmtop computer, a mobile device, a tablet computer, a notebook computer, a desktop computer, a workstation computer, a server, or the like, or an array of processors, microprocessors, central processing units, general purpose computers, super computers, personal computers, laptop computers, palmtop computers, mobile devices, tablet computers, notebook computers, desktop computers, workstation computers, servers, or the like.

A "server," as used in this disclosure, means any combination of software and/or hardware, including at least one application and/or at least one computer to perform services for connected clients as part of a client-server architecture. The at least one server application may include, but is not limited to, for example, an application program that can accept connections to service requests from clients by sending back responses to the clients. The server may be configured to run the at least one application, often under heavy workloads, unattended, for extended periods of time with minimal human direction. The server may include a plurality of computers configured, with the at least one application being divided among the computers depending upon the workload. For example, under light loading, the at least one application can run on a single computer. However, under heavy loading, multiple computers may be required to run the at least one application. The server, or any if its computers, may also be used as a workstation.

A "database," as used in this disclosure, means any combination of software and/or hardware, including at least one application and/or at least one computer. The database may include a structured collection of records or data organized according to a database model, such as, for example, but not limited to at least one of a relational model, a hierarchical model, a network model or the like. The database may include a database management system application (DBMS) as is known in the art. The at least one application may include, but is not limited to, for example, an application program that can accept connections to service requests from clients by sending back responses to the clients. The database may be configured to run the at least one application, often under heavy workloads, unattended, for extended periods of time with minimal human direction.

A "communications network," as used in this disclosure, means a wired and/or wireless medium that conveys data or information between at least two points. The wired or wireless medium may include, for example, a metallic conductor link, a radio frequency (RF) communication link, an Infrared (IR) communication link, telecommunications networks, an optical communication link, internet (wireless and wired) or the like, without limitation. The RF communication link may include, for example, WiFi, WiMAX, IEEE 802.11, DECT, 0G, 1G, 2G, 3G, 4G, 5G or future cellular standards, Bluetooth, Bluetooth Low Energy, NFC, ultrasound, induction, laser (or similar optical transmission) and the like.

A "computer-readable storage medium," as used in this disclosure, means any medium that participates in providing data (for example, instructions) which may be read by a computer. Such a medium may take many forms, including non-volatile media, volatile media, and transmission media. Non-volatile media may include, for example, optical or magnetic disks, flash memory, and other persistent memory. Volatile media may include dynamic random access memory (DRAM). Transmission media may include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read. The computer-readable medium may include a "Cloud," which includes a distribution of files across multiple (e.g., thousands of) memory caches on multiple (e.g., thousands of) computers.

Various forms of computer readable media may be involved in carrying sequences of instructions to a computer. For example, sequences of instruction (i) may be delivered from a RAM to a processor, (ii) may be carried over a wireless transmission medium, and/or (iii) may be formatted according to numerous formats, standards or protocols, including, for example, WiFi, WiMAX, IEEE 802.11, DECT, 0G, 1G, 2G, 3G or 4G cellular standards, Bluetooth, or the like.

A "network," as used in this disclosure means, but is not limited to, for example, at least one of a local area network (LAN), a wide area network (WAN), a metropolitan area network (MAN), a personal area network (PAN), a campus area network, a corporate area network, a global area network (GAN), a broadband area network (BAN), a cellular network, the Internet, the cloud network, or the like, or any combination of the foregoing, any of which may be configured to communicate data via a wireless and/or a wired communication medium. These networks may run a variety of protocols not limited to TCP/IP, IRC, SSL, TLS, UDP, or HTTP.

A term "sensor" shall be taken to mean an electronic, electrochemical, electromechanical, or Microelectromechanical systems (MEMs) device capable of pH sensing, $CO_2$ sensing, acoustic sensing, capacitance sensing, inductance sensing, temperature sensing, specific molecule sensing, or ambient color sensing and presenting the output of that sensing as an electrical signal which may then be read by complementary electronics. The aforementioned definition of "sensor" shall also be understood to include electronic devices designed for image capture disposed at either a single location or multiple locations. Image capture sensors shall include those responsive to the visible, IR, and UV spectrums. The aforementioned definitions of "sensor" shall also include paired emitters and receivers of energy including for instance illuminated LEDs paired with electronics to record and measure the light reflected by the surroundings and acoustic energy emitters such as speakers or piezoelectric paired with electronics to record the sound energy reflected by the surroundings. Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

Figure 1B:
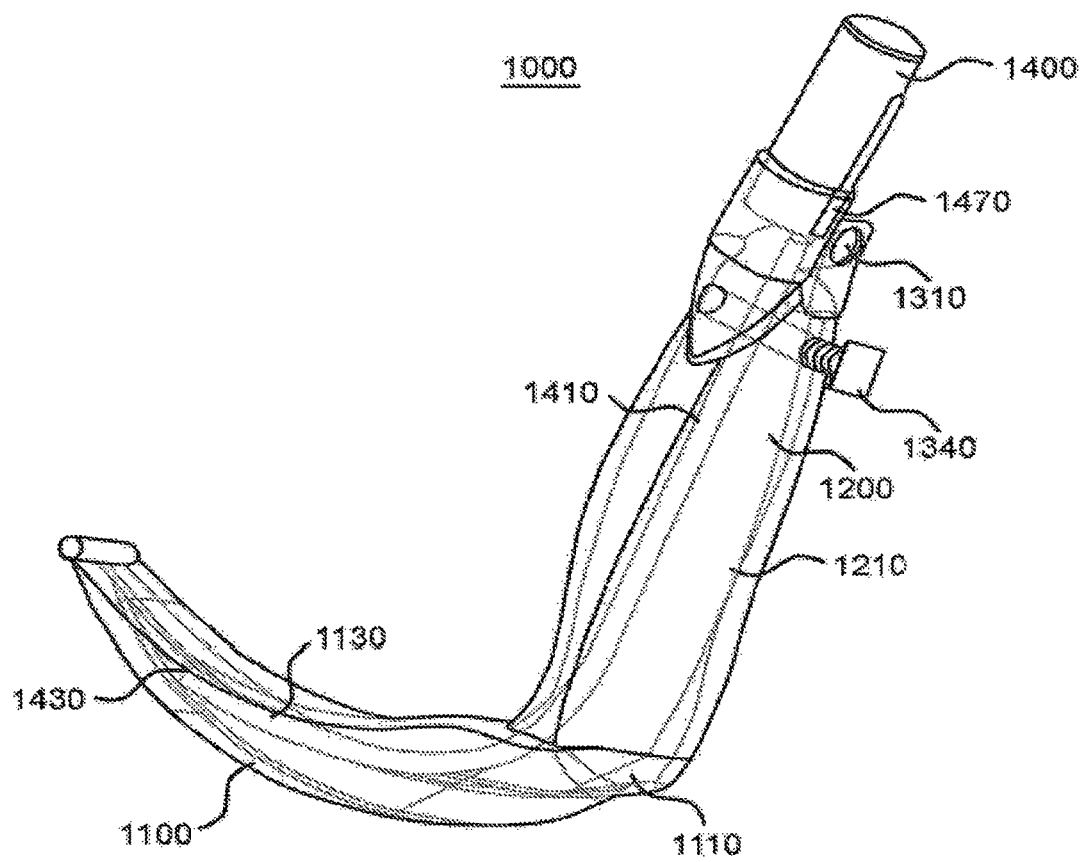
FIG. 1B shows a back perspective view of the improved laryngoscope of FIG. 1A.
Figure 2A:
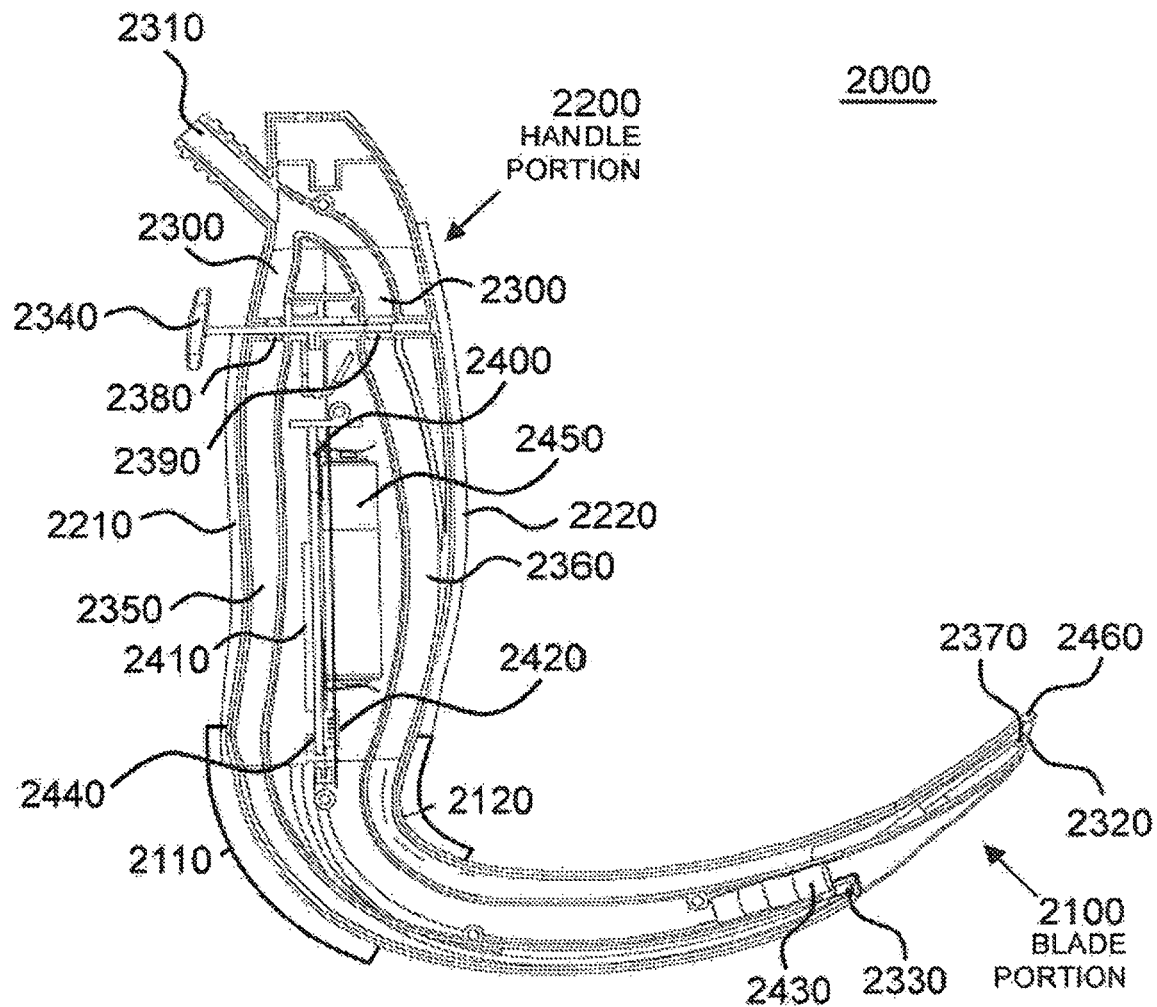
FIG. 2A shows an isometric wireframe view of another example of an improved laryngoscope that is constructed in accordance with the principles of the present disclosure.
Figure 2B:
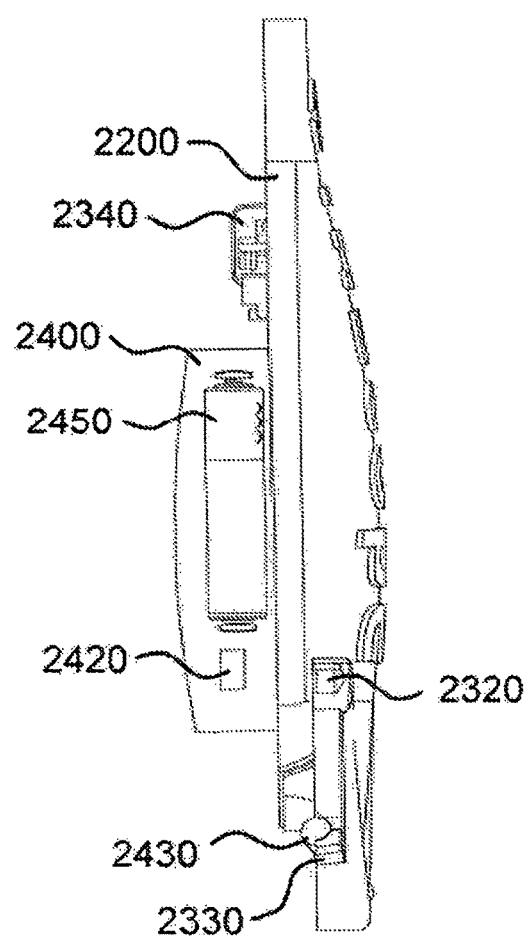
FIG. 2B shows another isometric wideframe view of the improved laryngoscope of FIG. 2A.
Figure 2C:
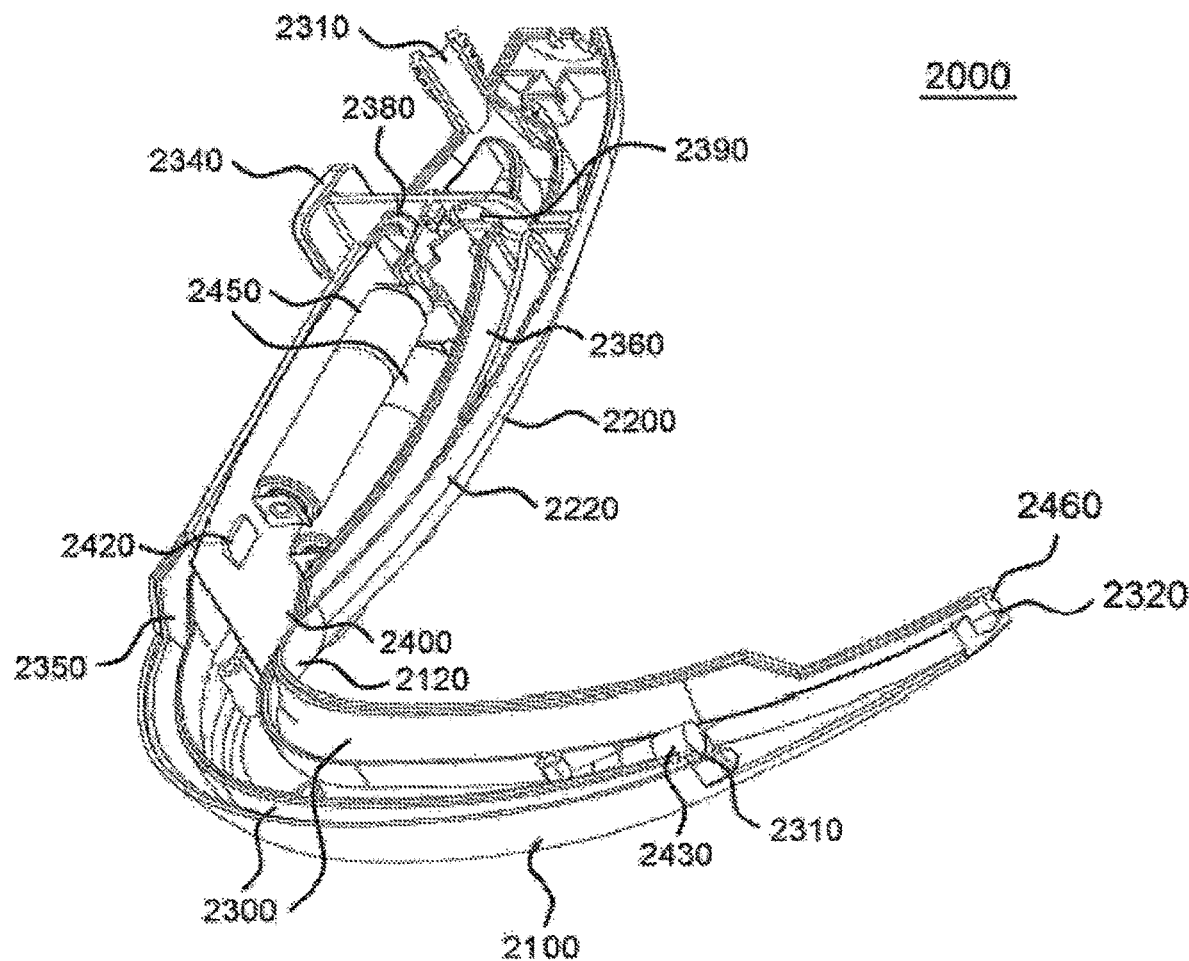
FIG. 2C shows an isometric wideframe view of the improved laryngoscope of FIG. 2A.
Figure 2D:
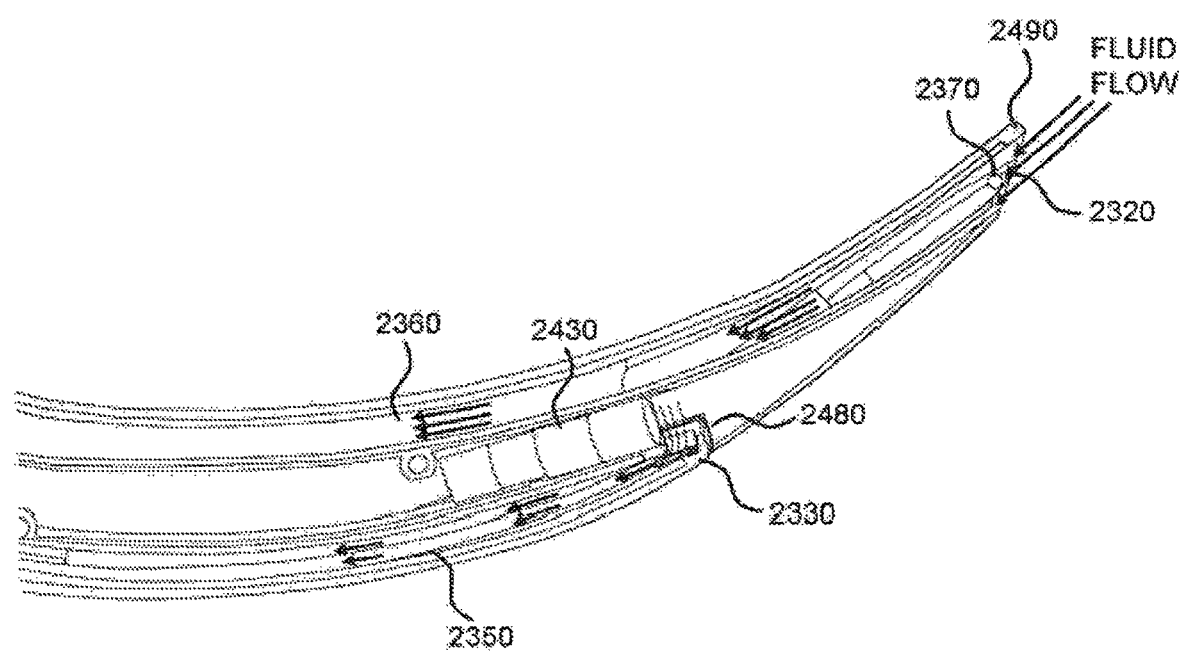
FIG. 2D shows an isometric wideframe view of blade portion of the improved laryngoscope.

Referring concurrently to FIGS. 1A and 1B, a laryngoscope 1000 includes a handle 1200, a blade 1100, at least one sensor 1430, and at least one fluid channel 1300, wherein the handle 1200 includes (a) a top portion that is configured to hold a removable electronic component module 1400 and (b) a bottom portion that is configured to be connected the blade portion 1100 at an intersection 1120, wherein the blade portion 1100 includes a proximal face 1110 and a distal tip 1490, wherein (a) the proximal face 1110 is configured to connect with the bottom portion of the handle 1200 and (b) the distal tip 1490 includes at least one distal fluid inlet 1320, wherein the at least one sensor 1430 is configured to be located near the distal tip 1490, wherein the distal tip 1490 includes at least one proximal fluid inlet 1330 near the at least one sensor 1430, and wherein the at least one fluid channel 1300 includes at least one fluid outlet 1310 that is configured to be in a fluid communication with (a) the at least one distal fluid inlet 1320 and (b) the at least one proximal fluid inlet 1330. In an embodiment of the present disclosure, the handle 1200 and the blade 1100 may be configured to be one single unit. In another embodiment of the present disclosure, the handle 1200 and the blade 1100 may be separate units that are conjoined by, e.g., screw, nail, fastener, glue, adhesive, and the like.

The laryngoscope 1000 may also include a valve system 1340 that is located near the at least one fluid outlet 1310 and is configured to control (or close) fluid communication between the at least one fluid outlet 1310 and the at least one distal fluid inlet 1320.

The laryngoscope 1000 may further include a flexible sensor tube 1410 that is configured to connect the removable electronic component module 1400 to the at least one sensor 1430 by a flexible sensor tube 1410 that passes through a sensor tube cavity 1130 within the handle 1200 and the blade portion 1100.

In an embodiment of the present disclosure, the laryngoscope 1000 may further include at least one fluid channel 1300 that extends internally from the top portion of the handle 1200 through the blade 1100 terminating in the at least one distal fluid inlet 1320 and the at least one proximal fluid inlet 1330, wherein the at least one proximal fluid inlet 1330 is located near (or at) the at least one sensor 1430, and wherein the at least one fluid channel 1300, the at least one distal fluid inlet 1320, and the at least one proximal fluid inlet 1330 are in fluid communication with the at least one fluid outlet 1310 which is located near (or at) the top portion of the handle 1200 via the at least one fluid channel 1300.

In one embodiment of the laryngoscope, the handle 1200 may include contacts 1470 and the blade 1100 includes an inductive sensing module 1460 near the distal fluid inlet 1320. The inductive sensing module 1460 may be formed from electrical leads or an inductive coil embedded into the area near the at least one distal fluid inlet 1320. When the removable electronic component module 1400 is coupled to the handle 1200, an electrical communication may be established between contacts 1470 on the handle 1200 and the inductive sensing module 1460. Upon the presence of certain capacitive or inductive states as reported by the at least one sensor 1430 that is configured to detect presence or absence of fluid near the distal tip 1490 of the blade 1100, the removable electronic module 1400 is able to activate or de-activate the valve system 1340, thereby evacuating the excess fluid.

According to further embodiments of the present disclosure, the electronic component module 1400 may include: (a) battery 1450 that provides power to the electronic component module 1400 (and the at least one sensor 1430 through the sensor tube 1410); (b) a data processing unit 1480 that processes data it received regarding fluid (or any other in vivo information) from the at least one sensor 1430 (c) a sensory data encoder 1440 that encodes data; and (a) network radio 1420 that is configured to receive the encoded data from the sensory data encoder 1440 and transmit said data to a remote device, a server, or a database. In an embodiment of the present disclosure, the sensory data encoder 1440 may be configured to receive instructions from, e.g., a system administrator, doctor, nurse, and the like, with regards to use of the laryngoscope 1000, such as, for example, begin or stop collecting fluid, transmit data regarding the fluid, turn on (or off) the power on the electronic component module 1400 (or the at least one sensor 1430), control recording of raw or analyzed data from the at least one sensor 1430, and the like.

In an embodiment of the present disclosure, the at least one sensor 1430 may be configured to detect pH, $CO_2$, acoustic, capacitance, inductance, temperature, specific molecule, binocular image, monocular image, arrayed image, or ambient color to be sent to the electronic component module for processing. The sensor may also generate light and measure frequency of light.

Referring now to FIGS. 2A, 2B, 2C, and 2D, another embodiment of laryngoscope 2000 is disclosed. The laryngoscope 2000 includes a handle 2200, a blade 2100, an electronic component module 2400, at least one sensor 2430, a fluid outlet 2310, at least one fluid channel 2360, a distal fluid inlet 2320, and a proximal fluid inlet 2330, wherein the handle 2200 includes: (a) a top portion that is configured to house (or enclose) a fluid outlet 2310 which protrudes from the handle 2200, (b) a bottom portion that is configured to connect with the blade 2100, (c) a distal handle face 2220 that is configured to house (or enclose) a distal fluid channel 2360 that is configured to extend internally to the distal fluid inlet 2320 for fluid communication and (d) a proximal handle face 2210 that is configured to house (or enclose) a proximal fluid channel 2350 that is configured to extend internally to the proximal fluid inlet 2330 for fluid communication; wherein the blade portion 2100 is configured to be joined to the bottom portion of the handle 2200 and further includes a proximal tip 2480 and a distal tip 2490; wherein (a) the proximal tip 2480 is located at (or near) the proximal fluid inlet 2330 and the at least one sensor 2430; and (b) the distal tip 2490 is located at (or near) the distal fluid inlet 2320; wherein the at least one sensor 2430 is housed within the blade portion 2100 and is further configured to be located near the distal tip 2490; and wherein the electronic component module 2400 is configured to be housed (or enclosed) inside the handle 2200 and fixedly (or removably) coupled between the top portion and the bottom portion of the handle 2200. In an embodiment of the present disclosure, the handle 2200 and the blade 2100 may be configured to be one single unit. In another embodiment of the present disclosure, the handle 2200 and the blade 2100 may be separate units that are conjoined by, e.g., screw, nail, fastener, glue, adhesive, and the like.

The laryngoscope 2000 may also include a valve system 2340 that is interposed in a channel 2470 near the fluid outlet 2310. The valve system 2340 may further be configured to control (or close) fluid communication between the fluid outlet 2310 and the distal fluid inlet 2320 and the proximal fluid inlet 2330. The valve system may open (or close) the fluid communication via e.g., fastening mechanism.

The laryngoscope 2000 may further include a flexible sensor tube (not shown) that is configured to connect the electronic component module 2400 to the at least one sensor 2430 by a flexible sensor tube that passes through a sensor tube cavity (not shown) within the handle 2200 and the blade portion 2100. This allows the at least one sensor 2430 to draw battery power from the electronic component module 2400 and/or transmit collected data to the electronic component module 2400. Alternatively, the at least one sensor 2430 may include its own battery source. The at least one sensor 2430 may also include a wireless transmitter that wirelessly transmits collected (or monitored) data to the electronic component module 2400 (or to a remote device, a server, a database, and the like) over a communications network. The at least one sensor 2430 may also transmit data via network radio 2420 that is part of (or separate from) the electronic component module 2400.

In one embodiment of the laryngoscope, the handle 2200 may include contacts (not shown) and the blade 2100 may include an inductive sensing module 2460 near the distal fluid inlet 2320. The inductive sensing module 2460 may be formed from electrical leads or an inductive coil embedded into the area near the distal fluid inlet 2320. When the electronic component module 2400 is removably (or fixedly) coupled to the handle 2200, an electrical communication may be established between contacts on the handle 2200 and the inductive sensing module 2460. Upon the presence of certain capacitive or inductive states as reported by the at least one sensor 2430 that is configured to detect presence or absence of fluid (or other factors, such as, e.g., pH, $CO_2$, acoustic, capacitance, inductance, temperature, specific molecule, binocular image, monocular image, arrayed image, ambient color, or the like) near the distal tip 2490 of the blade 2100, the removable electronic module 2400 is able to activate or de-activate the valve system 2340, thereby evacuating the excess fluid.

In another embodiment of the present disclosure, the proximal fluid inlet 2330 may, in addition to collecting bodily fluid or sample through the inlet, exert air or fluid to clean (or clear the obstructions in front of) the at least one sensor 2430 so that the at least one sensor 2430 can more clearly view or monitor in vivo. In yet another embodiment of the present disclosure, the liquid taken in from the distal fluid inlet 2320 may circulate through the distal fluid channel 2360 and the proximal fluid channel 2350 to eventually exit at the proximal fluid inlet 2330 to clear the proximal fluid inlet 2330 and thereby clean the at least one sensor 2430.

According to further embodiments of the present disclosure, the electronic component module 2400 may include: (a) battery 2450 that provides power to the electronic component module 2400 (and the at least one sensor 2430 through the sensor tube); (b) a sensory data encoder 2440 that encodes the raw data that it receives regarding monitored/collected fluid (or any other in vivo information) from the at least one sensor 2430 and transmit the encoded data to a data processing unit 2410; (c) the data processing unit 2410 that processes encoded data; and (d) a network radio 2420 that is configured to receive the processed data from the data processing unit 2410 and transmit the processed data to, e.g., a remote device, a server, a database, or the like. In an embodiment of the present disclosure, the network radio 2420 may be configured to receive instructions from, e.g., a system administrator, doctor, nurse, and the like, with regards to use of the laryngoscope 2000, such as, for example, begin or stop collecting fluid, transmit data regarding the fluid, turn on (or off) the power on the electronic component module 2400 (or the at least one sensor 2430), and the like. Such instructions may be carried out via a machine readable code that is embedded in e.g., the electric component module 2400, the at least one sensor 2430, the valve system 2340, and the like.

In an embodiment of the present disclosure, the at least one sensor 2430 may be configured to detect pH, $CO_2$, acoustic, capacitance, inductance, temperature, specific molecule, binocular image, monocular image, arrayed image, or ambient color to be sent to the electronic component module for processing. The sensor may also generate light and measure frequency of light.

In an optional embodiment, an inductive sensing module 2460 formed from electrical leads or an inductive coil may be embedded into the area near the distal fluid inlet 2490.

Figure 3A:
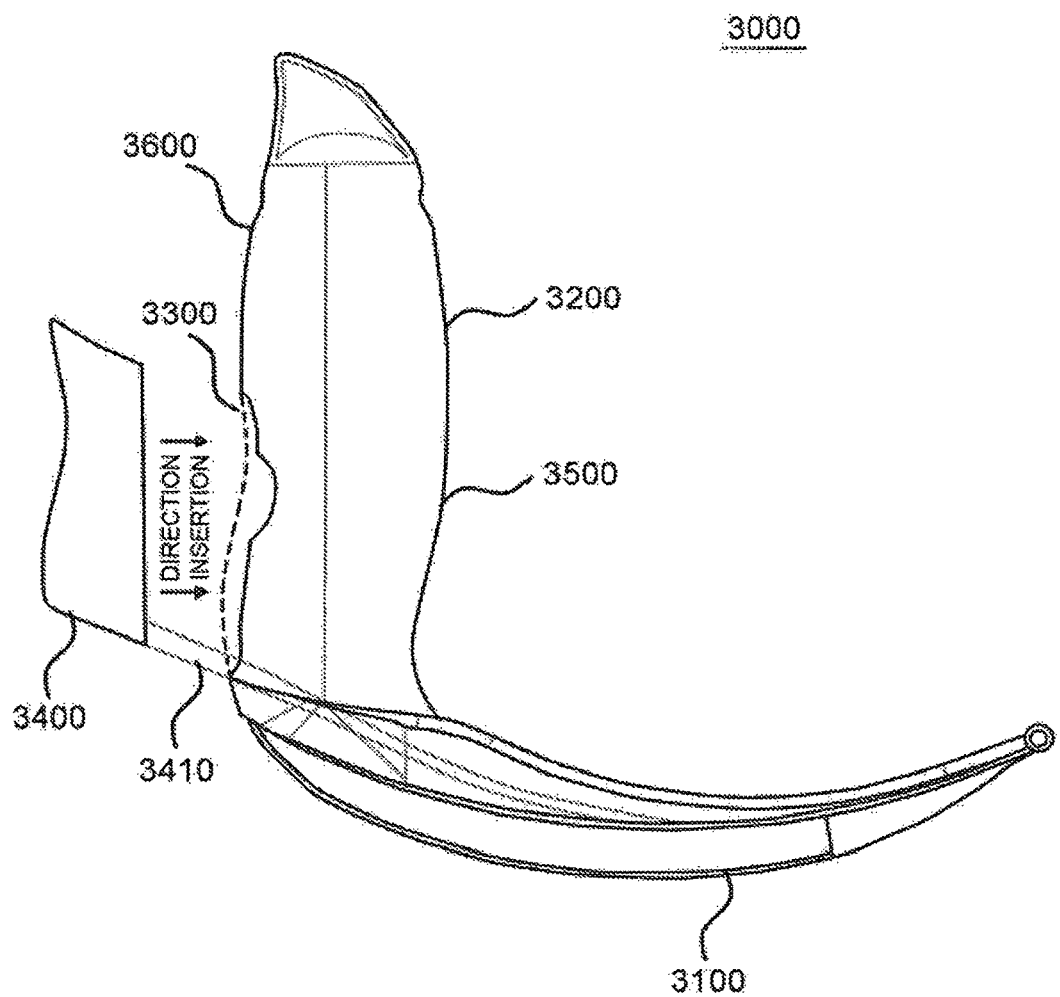
FIG. 3A shows a side perspective view of yet another example of an improved laryngoscope that is constructed in accordance with the principles of the present disclosure.
Figure 3B:
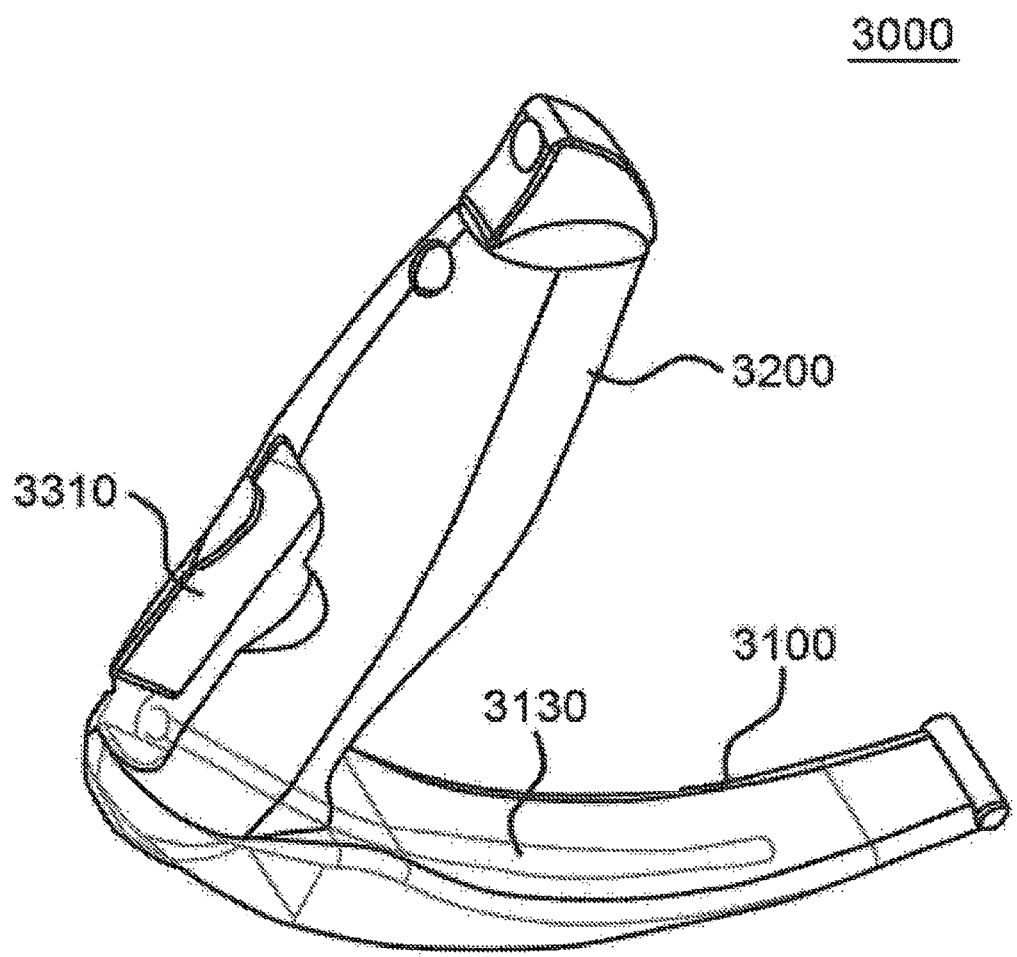
FIG. 3B shows an isometric wideframe view of the improved laryngoscope of FIG. 3A.

Referring now to FIGS. 3A and 3B together, yet another example of a laryngoscope 3000 is disclosed that is constructed in accordance with the present disclosure. The laryngoscope includes: a handle 3200 that has a top portion, a bottom portion, a proximal face 3600, and a distal face 3500; a blade 3100 that is attached to the bottom portion of the handle 3200 and protrudes outwardly therefrom in a substantially perpendicular angle in direction of distal face 3500, an electronic component module cavity 3310 that is disposed on the proximal face 3600 (face of the handle opposing the protruding direction of the blade 3100) that is configured to hold an electric component module 3400; a sensor tube cavity 3130 within the handle 3200 and the blade 3100 that is configured to extend from the electronic component module cavity 3310 towards edge of the blade 3100; at least one sensor (not shown) near edge of the blade 3100; and a sensor tube that extends within the sensor tube cavity 3110 to connect the at least one sensor with the electric component module 3400 for, e.g., power, data transmission, wireless or wired instructions, and the like.

In an embodiment of the present disclosure, the electronic component module door 3300 may include a removable faceplate (not shown) held in place by a spring-loaded live hinge molded into at least one edge of the electronic component module door 3300. Upon application of pressure to the hinge by an operator, the door 3300 may be optionally removed thereby exposing the electronic component module cavity 3310 sized and shaped to hold the complementary electronic component module 3400. When inserted into the cavity 3310, the portion of the electronic component module protruding from the handle substantially approximates the shape of the door 3300.

The laryngoscope 3000 may further include inlet(s), outlet(s), valve system, or other components as described in, e.g., FIGS. 1-2. The laryngoscope 3000 may further be configured to carry out method of collecting, transmitting, and/or analyzing fluid and related data as described in, e.g., FIGS. 1-2.

Figure 4:
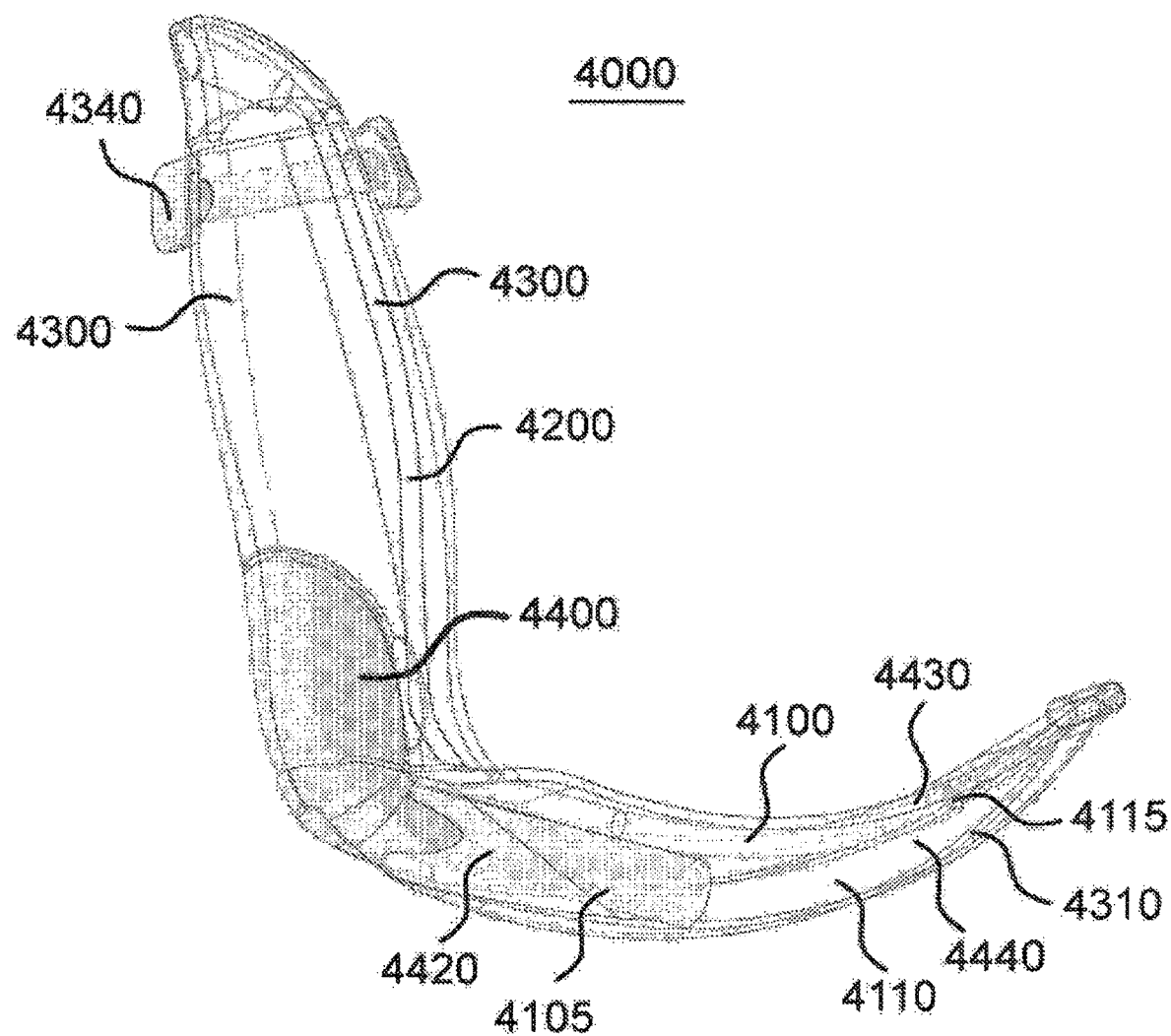
FIG. 4 shows an isometric wideframe view of yet another example of an improved laryngoscope that is constructed in accordance with the principles of the present disclosure.

Referring now to FIG. 4, yet another laryngoscope 4000 is disclosed that is in accordance with the principles of the present disclosure. The laryngoscope 4000 includes a handle 4200 with a top portion and a bottom portion; and a blade 4100 that is connected to the bottom portion of the handle 4200 and is further configured to protrude from the handle 4200 in a substantially perpendicular angle in a similar fashion as shown in, e.g., FIGS. 1-3.

The laryngoscope 4000 further includes an electronic component module 4400 that is sized and shaped to be optionally coupled at an intersection where the bottom portion of the handle 4200 and the blade 4100 meets.

The electronic component module 4400 may include a battery power source 4420 extending distally therefrom into a complementary cavity 4105 within the blade portion 3100.

The electronic component module 4400 may include a sensor tube 4440, which extends into a cavity 4110 in the blade 4100. The cavity 4110 may terminate in a window 4115 that is designed to allow the function of a sensor 4430 disposed at the tip of sensor tube 4420. If for instance the sensor 4430 is an acoustic sensor, image sensor, gas sensor, or fluid sensor, the window 4115 would be chosen from a material which allows that sensor to detect outside of the body of the blade 4100, such as, an acoustically transparent membrane, an optically transparent material, a gas-permeable membrane or mesh, or a fluid-permeable membrane or mesh respectively.

Figure 5A:
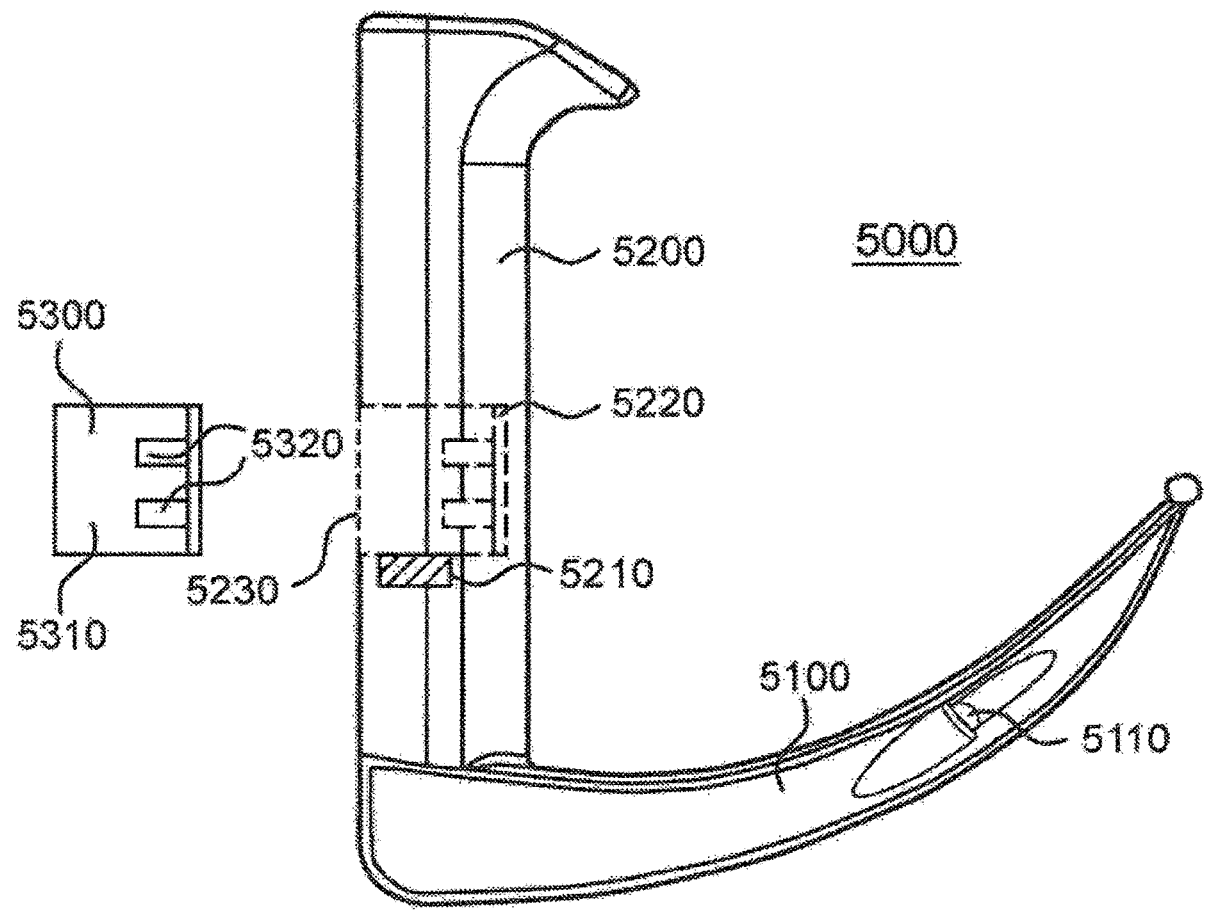
FIGS. 5A and 5B show an improved laryngoscope and its method of engagement with an electronic component module.
Figure 5B:
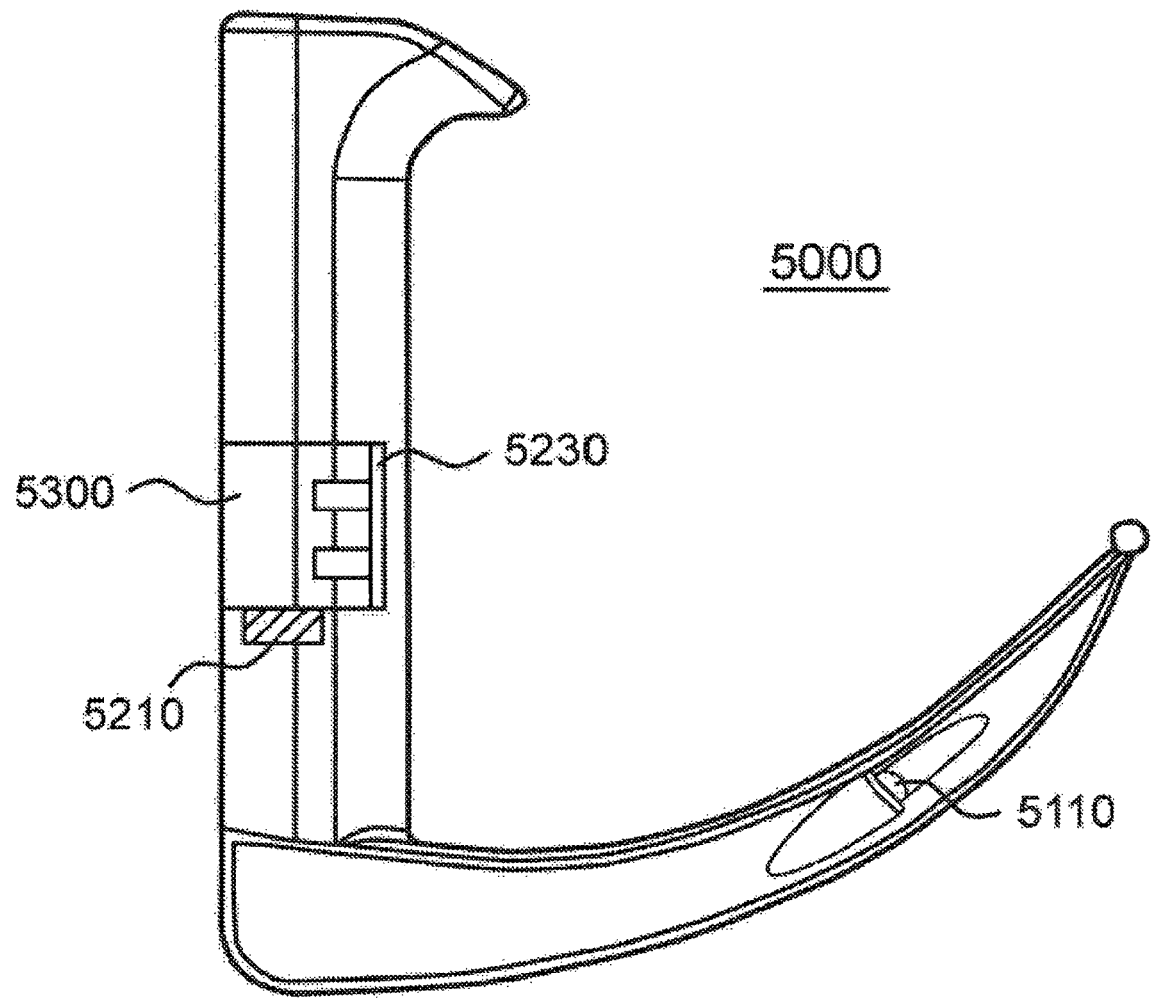

Referring now to FIGS. 5A and 5B concurrently, yet another example of an improved laryngoscope 5000 is disclosed. The laryngoscope 5000 includes a handle portion 5200 and a blade portion 5100 that are conjoined together in a similar way as shown in, e.g., FIGS. 1-4. The handle may include a sliding door 5230 that is operatively configured to be capable of sliding between the two configurations shown in FIGS. 5A and 5B as well as a cavity behind the sliding door 5230 occupied by an electronic contacts 5220 and a mechanical catch 5210. The electronic contacts 5220 are in electrical communication with at least one sensor 5110 that is disposed near the tip of the blade portion 5100. The mechanical catch 5210 may be a spring-loaded catchment sized and shaped to temporarily engage upon a complementary recess 5310 in an electronic component module 5300. The electronic component module 5300 may include an integral body housing and an electronics package along with an electronic contacts 5320.

When an operator urges electronic component module 5300 against door 5230 in the direction shown by the arrow in FIG. 5A, the door 5230 is displaced and electronic component module 5300 can be inserted into handle portion 5200 until catch 5210 engages upon recess 5310 and contacts 5320 and 5220 are in communication with one another. An example of such configuration is shown in, e.g., FIG. 5B. The electronics package within electronic component module 5300 may be configured to act as part of a larger overall system which (1) receives input from sensor 5110, (2) process that input into anatomical location information, (3) communicate the location information derived from that input to a user (or operator, doctor, and the like), (4) store the data, (5) transmit both the data and location information to, e.g., a remote device, a database, a server, administrative computer, and the like, and (6) take pre-determined action based on data derived from the information. The various functionalities (1)-(6) may selectively occur within the electronic component module 5000 or away from it on, e.g., a computer.

For example, if the sensor 5110 is a camera or other imager, the electronics package of certain embodiments of the present disclosure would include appropriate microprocessors to capture and condition the output of the image sensor as well as electronics for transmitting that output to a remote workstation (or a computer, a server, a database, and the like) over a physical or wireless connection via communications network. In such a configuration, the workstation would be further configured to identify anatomical landmarks such as tonsils, or vocal chords and communicate that information to an operator via a display or other user interface as shown in, e.g., FIGS. 9A, 9B, and 10.

In this example case, steps (1) and (5) may occur inside the electronic component module, while the remaining power and processor intensive steps (2), (3), and (4) may occur on the workstation (or a computer, a server, a database, and the like).

In an embodiment of the present disclosure, the laryngoscope may include a capacitive fluid sensor at tip of its blade. In this example, the electronic component module may include an indicator LED on its body (handle or blade) which illuminates when sufficient fluid is detected by the capacitive fluid sensor. The electronic component module may also be capable of transmitting a signal (via communications network) to a suction pump associated (or connected) with the laryngoscope to either activate or deactivate the pump based on pre-determined or user-configured sensor output thresholds. In this example, all of the steps (1)-(6) described above may be capable of being executed directly on the electronic component module.

Figure 6:
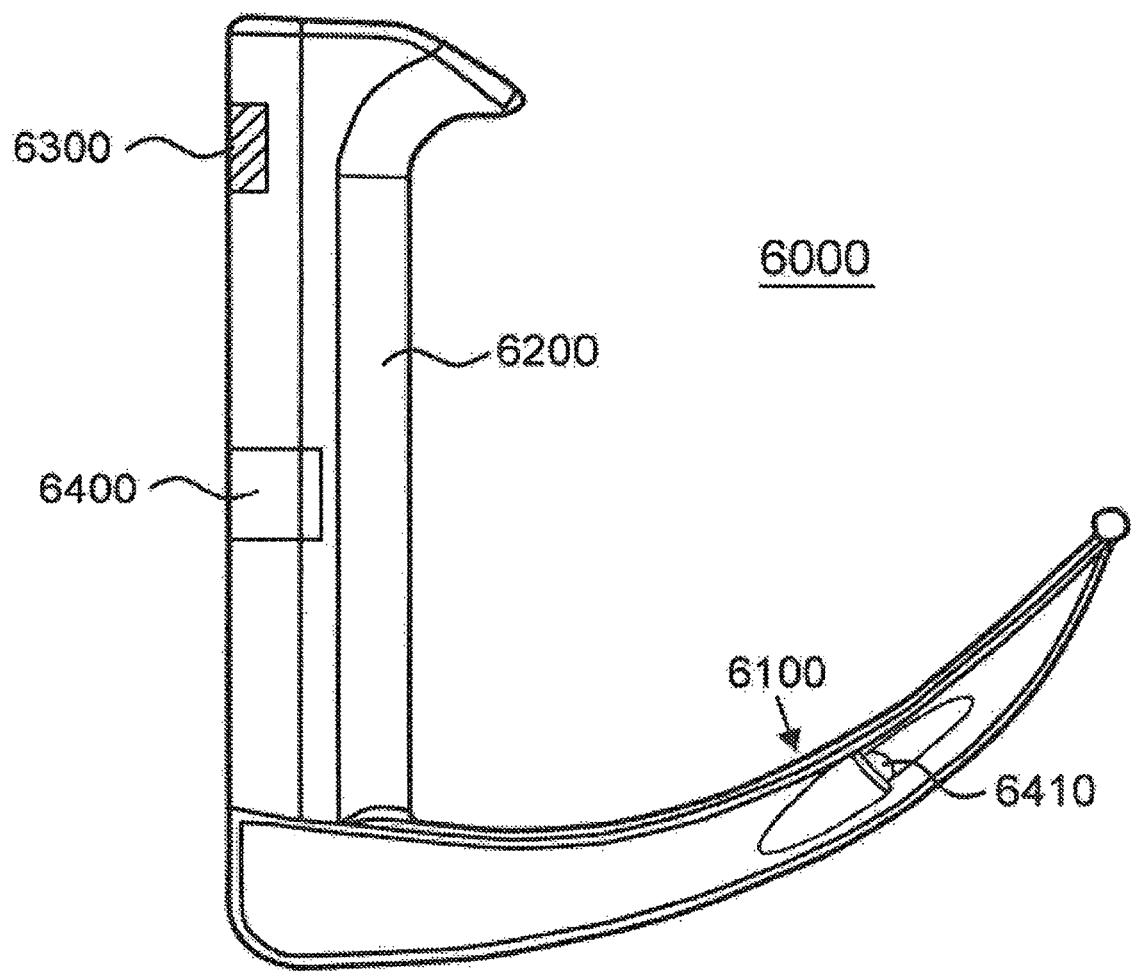
FIG. 6 shows an example of a side view of yet another example of an improved laryngoscope having LED disposed thereupon that is constructed in accordance with the principles of the present disclosure.

FIG. 6 shows yet another example of an improved laryngoscope 6000. The laryngoscope 6000 includes a handle portion 6200 and a blade portion 6100, with a sensor 6410 near the distal end of blade 6100 and a control module 6400 disposed in the handle 6200. The laryngoscope 6000 may further include a LED 6300 disposed in the handle 6200 which is in electronic communication with the sensor 6410 and control module 6400 to display assumed positional location thereon. For instance, if sensor 6410 is a pH sensor, then control module 6400 may be programmed to recognize or detect a threshold value of pH that is assumed for the mouth and trachea and a lower (or higher) pH value that is assumed to be present in other areas of the body, such as, e.g., esophagus. While the pH value is within the mouth/trachea parameters, the LED 6300 may display a certain color (e.g., green). The LED 6300 may then switch to another color (e.g., red) if the sensor 6410 acquires a reading that is indicative of another location, e.g., esophagus. Similar inferences regarding location could also be derived from a camera sensor which identifies specific geometries but then communicates that information as a simplified Boolean value communicated to the operator of whether the intubation is proceeding successfully.

Figure 7:
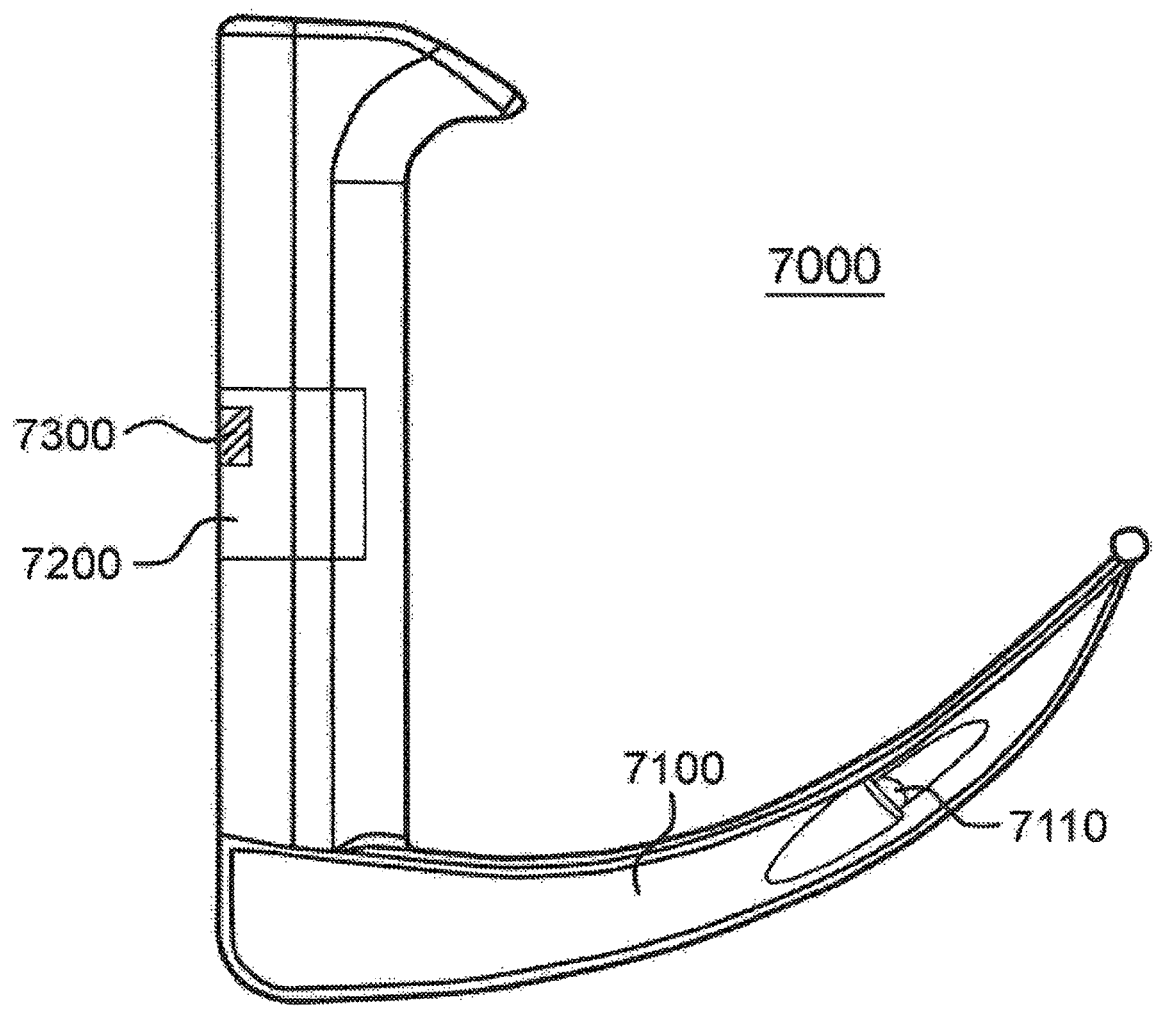
FIG. 7 shows a side view of yet another example of an improved laryngoscope having a speaker disposed upon the body thereof that is constructed in accordance with the principles of the present disclosure.

FIG. 7 shows an example of an improved laryngoscope 7000 that is constructed in accordance with the principles of the present disclosure. The laryngoscope 7000 is shown having a laryngoscope 7100, an electronic component module 7200, and an acoustic speaker 7300 disposed upon the body thereof. According to certain embodiments of the present disclosure, the algorithms (or programming) within the electronic component module 7200 may control the output of speaker 7300 to provide useful information to the operator (e.g., doctor, nurse, and the like) of the device. This may be direct information from the sensor 7110, including for instance, directly correlating a tone outputted by the speaker with, e.g., concentration of $CO_2$, pH, oxygen, or the like, that is identified by the sensor. The output may also be secondary information derived from other forms of sensing including for instance feature-identification type image processing to yield guidance such as "move the blade of the laryngoscope caudally," and the like.

Figure 8:
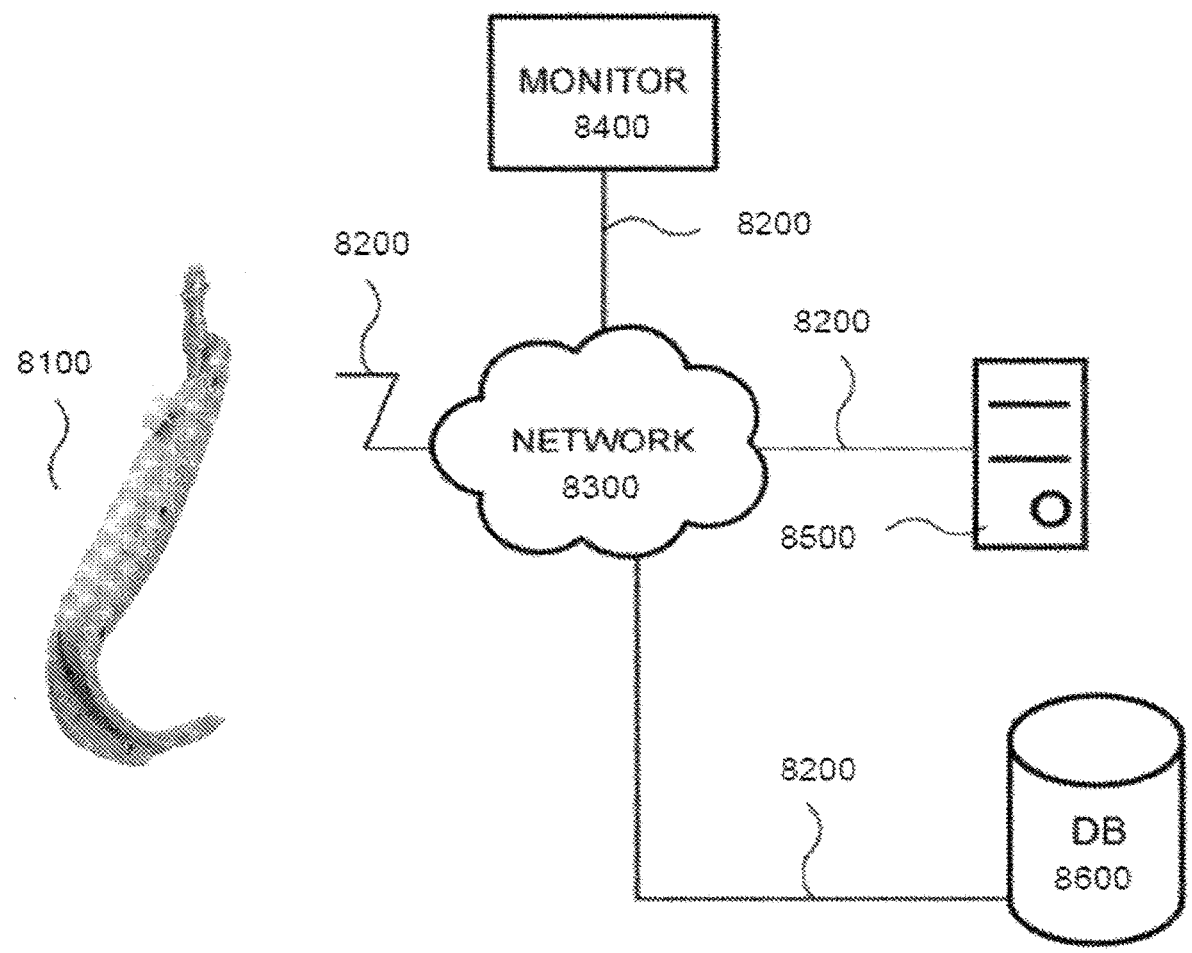
FIG. 8 shows an example of a system for collecting sensory data from an improved laryngoscope that is constructed in accordance with the principles of the present disclosure.

FIG. 8 shows an example of a system 8000 that is constructed according to the principles of the disclosure that provides use of presently disclosed laryngoscope to a treatment site of a patient, and receiving and carrying out wireless transmission of instructions, such as, for example, begin/end viewing, begin/end aspiration, apply treatment, transfer collected data to another location via communications network, and the like. The system 8000 includes at least one laryngoscope 8100, a network 8300, a monitor (e.g., a system manager) computer (or computing device) 8400, a hosted server (or computer) 8500, and a database 8600, all of which may be coupled to each other via communication links 8200. For instance, the hosted server 8500 and database 8600 may be connected to each other and/or the network 8300 via one or more communication links 8200. The at least one laryngoscope 8100 and the monitor computer 8400 may be coupled to the network 8300 via communication links 8200. The at least one laryngoscope 8100 may be used by, for example, an authorized user (e.g., doctor, nurse, or the like) of a patient to whom t at least one laryngoscope 8100 is being used. Once at least one laryngoscope 8100 collects liquid, said liquid may then transferred immediately to aerobic and/or anaerobic sterile tubes for microbiologic analysis.

In an embodiment of the present disclosure, the at least one laryngoscope 8100 may send transmit data collected from the patient via its sensor (as shown in, e.g., FIGS. 1-7) to the monitor computer 8400, the hosted server 8500, or the database 8600 for e.g., viewing, storage, analysis, and the like. Such viewing of the data may be configured to be displayed on a graphic user interface on, e.g., the monitor computer 8400, the hosted server 8500, or the database 8600. The data may be shown as, e.g., body parts, from the sensor of the at least one laryngoscope 8100 which is then analyzed to include an overlay of augmented reality (identifying different body parts) from the stored data or instructions in the system 8000 as shown in, e.g., FIGS. 9A, 9B, 10A, and 10B.

Figure 11:
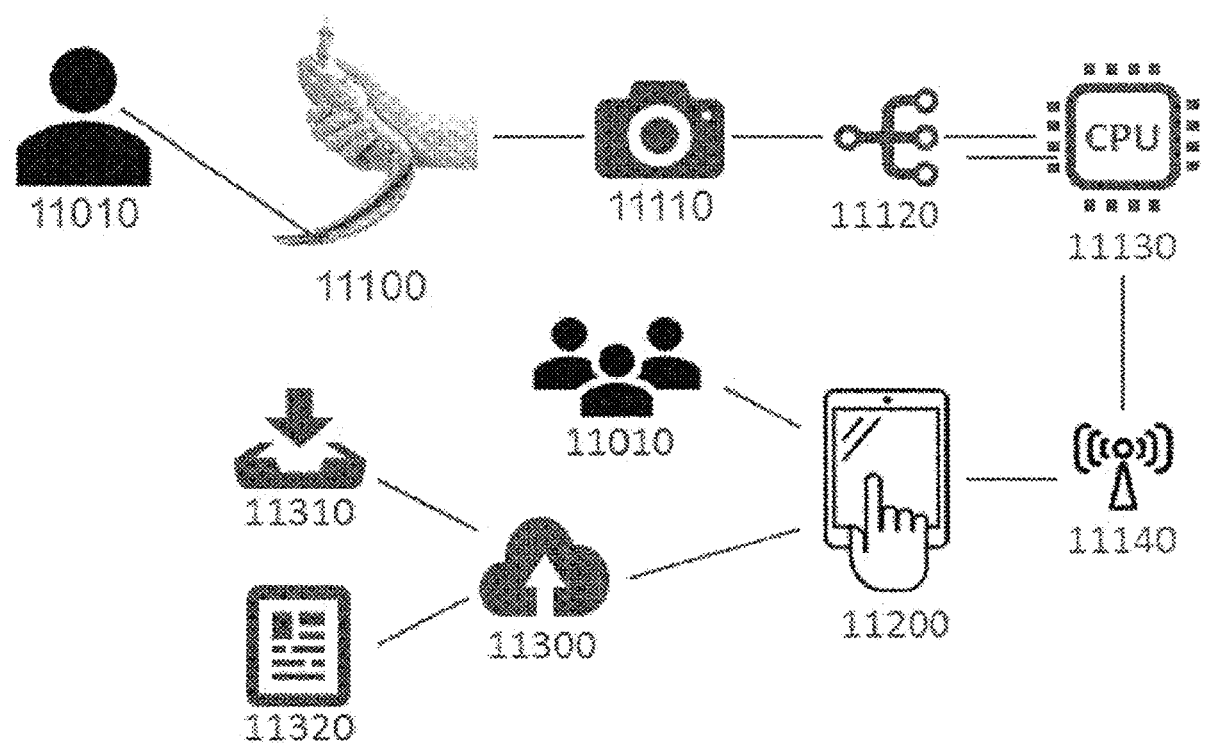
FIG. 11 shows an example of a system for collecting sensory data from an improved laryngoscope that is constructed in accordance with the principles of the present disclosure.
Figure 12:
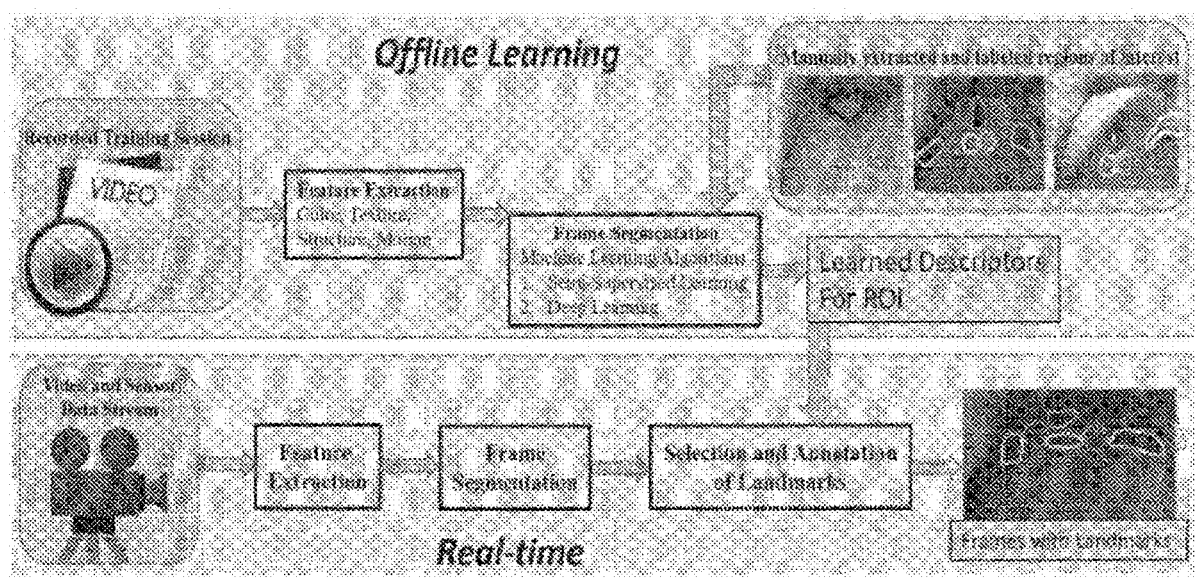
FIG. 12 shows an example of learning process facilitated by an improved laryngoscope that is constructed in accordance with the principles of the present disclosure.

The collected data from the at least one laryngoscope 8100 may also include pH, $CO_2$, acoustic, capacitance, inductance, temperature, specific molecule, binocular image, monocular image, arrayed image, or ambient color in the patient's body where the at least one laryngoscope 8100 is placed. The collected data may further be compiled and analyze for detecting certain factors in the patient's body, such as, for example, changes in pH, Oxygen, blood, and the like. The compiled and analyzed data may serve as a baseline for detecting certain bodily anomalies or be used to predict certain bodily ailments. Furthermore, such data may be used in conjunction with a machine learning algorithms stored in the monitor computer 8400 (or the hosted server 8500, the database 8600, or the at least one laryngoscope 8100) to identify certain bodily features (e.g., molar, tonsil, larynx, or the like) which can be helpful in guiding the at least laryngoscope to a correct location as shown in, e.g., FIGS. 9A, 9B, 10A, and 10B. An example of such use of the data is also shown in FIGS. 11 and 12.

Additionally, the at least one laryngoscope 8100, the monitor computer 8400, the hosted server 8500, and the database 8600 may each include a computer-readable medium including a computer program that may be executed to carry out the processes disclosed herein. The computer-readable medium may include a code section or code segment for performing each step disclosed herein. Few examples of these steps are shown in FIGS. 8 and 11-12.

Figure 9A:
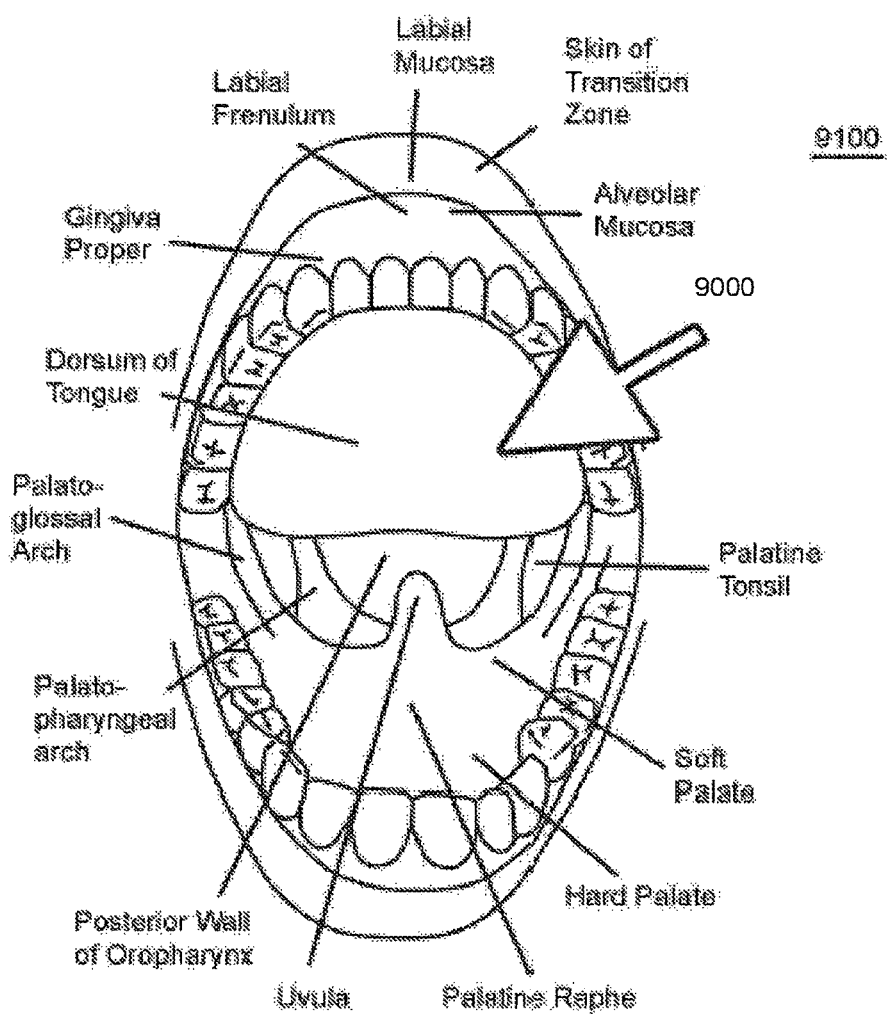
FIG. 9A shows an example of an augmented reality overlay that is constructed in accordance with the principles of the present disclosure.

FIG. 9A shows an example of an augmented reality overlay 9100 that is constructed in accordance with the principles of the present disclosure. As shown, the majority of the view on a screen may be taken directly from the image sensor in the presently disclosed laryngoscope. Such image may display anatomical landmarks such as the molars, tonsils, and uvula. According to one embodiment of the present disclosure, an overlay 9000 is provided, with the overlay showing the correct path for the intubation. The location and direction of overlay 9000 relative to the other elements in the field of view that may be calculated by using image processing technology to identify known anatomical landmarks such as those listed herein.

Figure 9B:
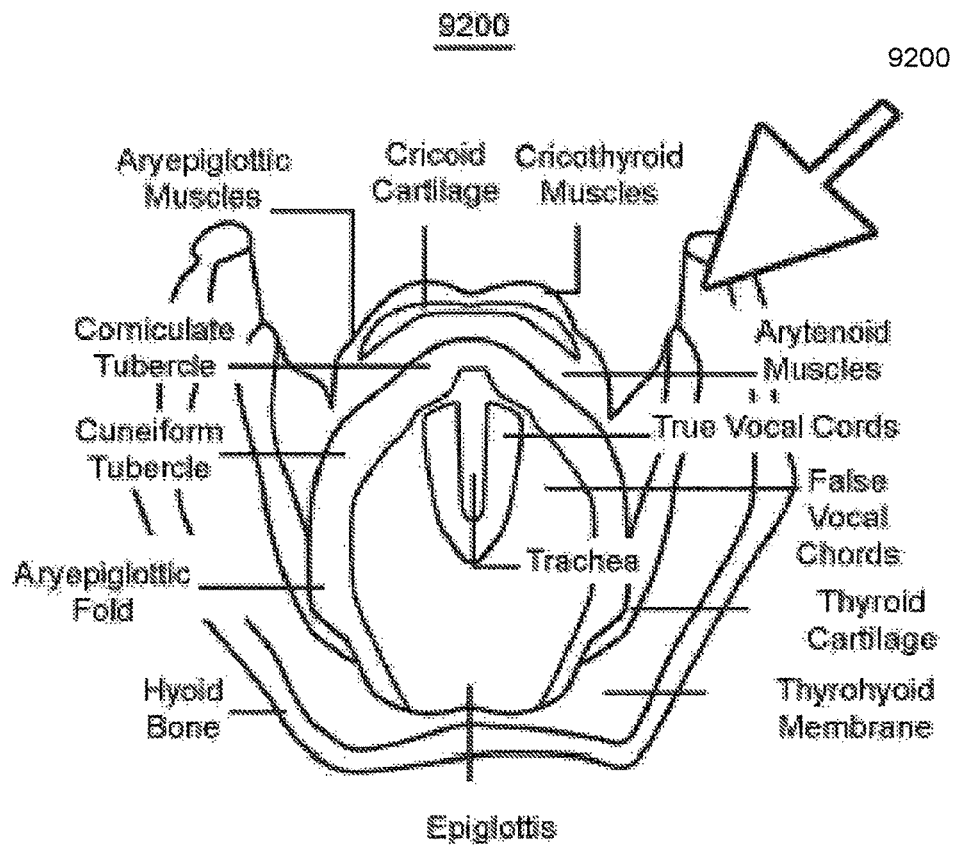
FIG. 9B shows a further example of an augmented reality overlay that is constructed in accordance with the principles of the present disclosure.

FIG. 9B shows an exemplary view is shown wherein the junction of the esophagus and trachea is visible and highlighted 9200 by the algorithm using an "arrow" overlay. According to certain embodiments of the present disclosure, this identification may take place by the use of eco-location or other reflected energy type sensing so as to identify the two channels whose depth is greater than that of the surrounding tissue.

Figure 10:
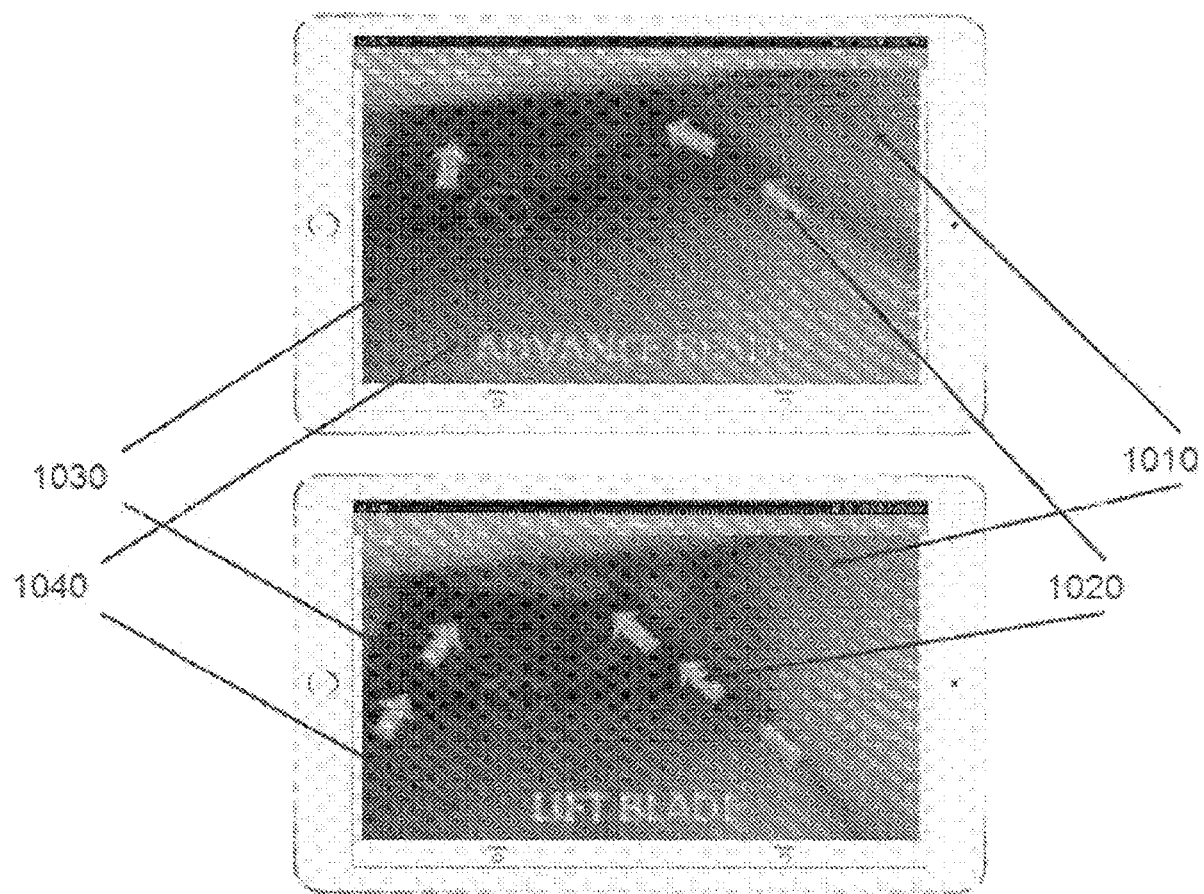
FIG. 10 shows yet another example of an augmented reality overlay shown on a remote device that is constructed in accordance with the principles of the present disclosure.

In a similar mechanism as shown in, e.g., FIGS. 9A and 9B, FIG. 10 shows an example of an augmented reality overlay that is imposed by algorithm (or calculation, pre-stored data, and the like) of the disclosed system. As shown, the augmented reality overlay can be shown on a remote device, such as, for example, a personal computer, a tablet, a smart phone device, and the like. The augmented reality overlay may direct the disclosed laryngoscope to a preferred direction via an arrow(s) overlay 1020 and also discourage certain direction via a symbol 1030. Such indicator of preferred or discouraged direction of the laryngoscope may also be indicated via a light or acoustic sound as previously disclosed herein.

FIG. 11 shows an example of the flowchart 11000 that is constructed according to the principles of the disclosure that provides use of presently disclosed laryngoscope in a patient. The laryngoscope 11,100, which includes a camera (or any other sensor) 11,110 that is electrically connected via electrical wire (or communications network) 11,120 to a CPU 11,130 and a radio 11,140, may by a user (e.g., doctor, nurse, or the like) 11,090 on a patient. Once the camera 11,110 collects data (e.g., picture) in vivo using the camera 11,110, the collected data may then be sent via the radio 11,140 to a remote device (or server, database, and the like) 11,200 via communications network. Once the collected data is received by the remote device 11,200, the collected data may then be viewed by other authorized users 11,010 or be uploaded into cloud server 11,300 (or a database) from which the data may be downloaded onto an authorized user's hard drive 11,310 or be sent to an electronic health record 11,320.

FIG. 12 shows another example of a flowchart for configuring the system as disclosed herein. In the top (offline learning) process recorded video sessions of successful intubations are played through, with an experienced operator manually highlighting relevant anatomical features while a machine learning algorithm in, e.g., laryngoscope, server, remote device, database, or the like, observes and attempts to differentiate the anatomical features from one another. Eventually, the machine learning algorithm may be able to identify there relevant anatomical features in the feed from a camera on the laryngoscope during a live intubation and use the knowledge of the presence and location of these features as guidance for an operator via the various forms of user feedback as shown in, e.g., FIGS. 9A, 9B, 10, and 11.

In another embodiment of the present disclosure, the disclosed laryngoscope, method, and system may be used in endotracheal tubes, laryngeal mask airway devices, supraglottic airway devices, combitubes, and other bodily cavities.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

Various embodiments of the invention are described herein. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A laryngoscope comprising;
  a handle comprising a top portion, a bottom portion, and at least one outlet;
  a blade with a distal tip and a proximal portion wherein the proximal portion is connected to the bottom portion of the handle;
  at least one fluid channel that is configured to extend through at least a portion of cross-section of the handle and the blade;
  at least one sensor that is located between the proximal portion and the distal tip of the blade and further configured to detect raw data once intubated in a patient;
  an electronic component module;
  a sensor tube cavity within the handle and the blade that is configured to extend from the electronic component module to the at least one sensor; and
  a flexible sensor tube that is configured to connect the electronic component module to the at least one sensor in order to transmit data from the at least one sensor to the electronic component module,
  wherein the flexible sensor tube passes through the sensor tube cavity within the handle and the blade,
  wherein the blade is configured to protrude outwardly at a substantially perpendicular angle from the handle to the distal tip,
  wherein the blade further comprises:
    (a) at least one inlet near the distal tip; and
    (b) at least one inlet between the distal tip and the proximal portion,
  wherein the electronic component module is sized and shaped to be coupled to the bottom portion of the handle,
  wherein the electronic component module comprises integrated circuitry which provides at least one functionality of: pH sensing, $CO_2$ sensing, acoustic sensing, capacitance sensing, inductance sensing, temperature sensing, specific molecule sensing, binocular image sensing, monocular image sensing, arrayed image sensing, ambient color sensing, USB video device class (UVC), generating light and measuring a frequency of light that is reflected by its surroundings, or any combination thereof, and
  wherein the at least one outlet, the at least one inlet near the distal tip, the at least one inlet between the distal tip and the proximal portion, and the at least one fluid channel, are configured to be in fluid communication with each other.

2. The laryngoscope of claim 1, wherein the raw data comprises at least two of: video file, pH level, $CO_2$ level, temperature, specific molecule, sound of trachea, lower pH of esophagus, and UV reflectivity of vocal chords.

3. The laryngoscope of claim 1, further comprising at least one valve that is located within the handle and configured to control the fluid communication between the at least one inlet, the at least one outlet, and the at least one fluid channel.

4. The laryngoscope of claim 1, further comprising a sensor cavity within the handle and the blade that is configured to extend from the electronic component module to the at least one sensor.

5. The laryngoscope of claim 1, wherein the raw data detected by the at least one sensor comprises at least one selected from the group of: pH, $CO_2$, acoustic, capacitance, inductance, temperature, and specific molecule.

6. The laryngoscope of claim 1, wherein the electronic component module further comprises:
  (a) a sensory data encoder that encodes the raw data that it receives from the at least one sensor and transmit the encoded data to a data processing unit, the raw data including temperature data, binocular image data, and ambient color data;
  (b) the data processing unit that processes the encoded data; and
  (c) a network radio that is configured to receive the processed data from the data processing unit and transmit the processed data to an external source.

7. The laryngoscope of claim 6, wherein the external source comprises a remote device coupled to a server.

8. The laryngoscope of claim 6, wherein the network radio is configured to receive instructions from a user with regards to use of the laryngoscope.

9. The laryngoscope of claim 8, wherein the instructions are associated with: begin collecting fluid, stop collecting the fluid, slow down the fluid communication, transmit the processed data, turn on the power on the electronic component module, and turn off the power on the electronic component module.

10. The laryngoscope of claim 1, wherein the handle further comprises contacts.

11. The laryngoscope of claim 10, wherein the blade further comprises an inductive sensing module near the at least one inlet, the inductive sensing module being configured to confirm a presence or absence of fluid determined by the electronic component module.

12. The laryngoscope of claim 11, wherein the inductive sensing module comprises at least one selected from the group of: electrical leads, and inductive coil.

13. The laryngoscope of claim 12, wherein the contacts and the inductive sensing module are configured to establish electrical communication when the electronic component module is attached to the handle.

14. The laryngoscope of claim 1, wherein the electronic component module is configured to be removable from the handle.

15. The laryngoscope of claim 1, wherein the at least one inlet between the distal tip and the proximal portion is located in close proximity to the at least one sensor.

16. The laryngoscope of claim 15, wherein the at least one inlet between the distal tip and the proximal portion is configured to exert air in order to clean the at least one sensor.

17. The laryngoscope of claim 15, wherein the at least one inlet between the distal tip and the proximal portion is configured to exert fluid that circulates in the laryngoscope via the at least one fluid channel in order to clean the at least one sensor.

18. The laryngoscope of claim 1, wherein the integrated circuitry contains at least one integrated wireless communication radio.

19. The laryngoscope of claim 18, wherein the at least one integrated wireless communication radio is configured to provide at least one functionality of 2.4 ghz wifi frequency, 5.0 ghz wifi frequency, Bluetooth, analogue data radio, 3g mobile data network, 4g mobile data network, 4g LTE mobile data network, and 5g mobile data network connectivity.

20. The laryngoscope of claim 18, wherein the integrated circuitry comprises at least one selected from the group of: onboard circuitry for amplifying output of the at least one sensor, onboard circuitry for conditioning the output of the at least one sensor, onboard circuitry for converting the output of the at least one sensor into a machine-readable format, onboard circuitry for transmitting the output of the at least one sensor to a remote device distinct from the laryngoscope via a physical wire, onboard circuitry for transmitting the output of the at least one sensor to a remote device distinct from the laryngoscope via the at least one integrated wireless communication radio, and onboard circuitry for transmitting the output of the at least one sensor to a remote device distinct from the laryngoscope via a communications network.

21. The laryngoscope of claim 2, wherein the electronic component module provides at least one data processing unit that is configured to provide at least one functionality of: hardware video encoding, general data processing, firmware storage and management, data encryption, audio encoding, visible and invisible spectrum light analysis, current analysis, image depth processing, or any combination thereof.

22. The laryngoscope of claim 21, wherein the at least one data processing unit utilizes at least one architecture of: Reduced Instruction Set Computer (RISC), Microprocessor without Interlocked Pipeline Stages (MIPS), Advanced RISC Machine (ARM), ARM 32 bit (AArch32), ARM 64 bit (AArch64), Single instruction multiple data (SIMV), Single instruction multiple threads (SIMT), Multiple instruction streams multiple data streams (MIMD), x86, or x86 Atom, or any combination thereof.

23. The laryngoscope of claim 22, wherein the at least one data processing unit encodes the raw data to at least one codec standard of: MJPEG, H.264, HEVC, H.265, or MPEG-4, or any combination thereof.

24. The laryngoscope of claim 21, wherein the raw data is encoded using an integrated hardware encoder.

25. The laryngoscope of claim 1, wherein the integrated circuitry comprises an onboard battery for power consumption needs of the at least one sensor.

26. The laryngoscope of claim 1, wherein the electronic component module includes a distinct conductor for receiving power from a device distinct from the laryngoscope.

27. The laryngoscope of claim 1, further comprising at least one selected from the group of: LED, and lighting conductor.

28. The laryngoscope of claim 27, wherein the LED is configured to function independently from the electronic component module.

29. The laryngoscope of claim 27, wherein the electronic component module is configured to draw current from at least one selected from the group of: the LED, and the lighting conductor.

30. The laryngoscope of claim 1, wherein the electronic component module is configured to be sized and shaped to be coupled to the handle.

31. The laryngoscope of claim 1, wherein the electronic component module is configured to be coupled to the laryngoscope via a door disposed upon the handle, thereby exposing a cavity therein.

32. The laryngoscope of claim 31, wherein the coupling of the door to the handle is selected from one of, a removable door, a sliding door, a mechanically hinged door, or a live hinged door.

33. The laryngoscope of claim 1, wherein the handle comprises a movable entry face on outer surface of the handle, such that when the electronic component module is urged against an entry face, the entry face and the electronic component module are translated into the handle until the electronic component module is coupled to a complementary engagement mechanism disposed within the handle, thereby mechanically coupling the electronic component module to the handle.

34. The laryngoscope of claim 1, wherein the blade is hinged and thereby capable of being configured as either a traditional or high-angle laryngoscope.

35. The laryngoscope of claim 34, wherein the hinging is modulated by a presence of the electronic component module.

36. The laryngoscope of claim 34, wherein the hinging is modulated by an absence of the electronic component module.

37. The laryngoscope of claim 34, wherein the hinging is modulated upon detection of excess fluid by the at least one sensor.

38. The laryngoscope of claim 34, wherein the hinging is modulated upon detection of abnormal anatomy inside the patient by the at least one sensor.

39. The laryngoscope of claim 1, wherein the specific molecule sensing functionality is achieved using the at least one sensor that is configured to recognize at least one of $O_2$, $N_2$, CO2, HCl, NaCl, and KCl.

40. The laryngoscope of claim 39, wherein the at least one sensor comprises: a contact sensor, a sensor for measuring present ambient gasses, or any combination thereof.

41. The laryngoscope of claim 1, wherein the at least one inlet between the distal tip and the proximal portion is oriented so as to clear the at least one sensor when the at least one sensor is obscured by fluid or tissue by applying a vacuum to the at least one outlet.

42. The laryngoscope of claim 2, wherein the electronic component module is capable of creating a visual feedback that identifies at least one anatomic marker inside the patient based on the raw data detected by the at least one sensor.

43. The laryngoscope of claim 42, wherein the at least one anatomic marker comprises: molars, soft palate, palatoglossal arch, uvula, palatine tonsil, palatopharyngeal arch, oropharynx, epiglottis, esophagus, glottis, cuneiform tubercle, conciculate tubercle, true vocal chords, false vocal chords, open vocal chords, closed vocal chords, or any combination thereof.

44. The laryngoscope of claim 42, wherein the electronic component module is capable of integrating the raw data from more than one of the at least one sensor to improve a certainty that the blade is in a given anatomical marker inside the patient.

45. The laryngoscope of claim 42, further comprising at least one of the following visual display to display the visual feedback: illuminated LED, a selectively illuminated LED array, a non-reflective e-ink style display, and a reflective LCD style display.

46. The laryngoscope of claim 42, wherein the electronic component module is configured to transmit the visual feedback to at least one selected from the group of: a remote device, a server, a database, and a system computer.

47. The laryngoscope of claim 46, wherein the visual feedback is provided as an overlay atop a live image from a camera near the distal tip of the blade.

48. The laryngoscope of claim 47, wherein the visual feedback is provided by providing a live wireframe style outline of anatomical features and path which the blade should follow inside the patient.

49. The laryngoscope of claim 42, wherein the visual feedback is displayed in a user interface to assist a user to guide the laryngoscope inside the patient for a path to successful intubation.

50. The laryngoscope of claim 1, wherein the electronic component module uses a Linux Embedded Development Environment (LEDE) to manage the integrated circuitry.

51. The laryngoscope of claim 1, wherein the arrayed image sensing is associated with two or more image sensors spaced from each other.

52. A system for intubation of a laryngoscope comprising:
    the laryngoscope that measures and transmits at least one output signal using a network radio:
    a computing device configured to (i) receive the at least one output signal from the laryngoscope via the network radio and cii) display the at least one output signal in real-time; and
    a graphical user interface on the computing device that allows a user to view and customize options for monitoring the at least one output signal,
    wherein the laryngoscope and the computing device are communicatively connected to each other via a communications network,
    wherein the network radio is configured to receive instructions from the user with regards to use of the laryngoscope via at least one network signal transmitted from the computing device, and
    wherein the laryngoscope comprises:
        a handle comprising a top portion, a bottom portion, and at least one outlet a blade with a distal tip and a proximal portion wherein the proximal portion is connected to the bottom portion of the handle;
        at least one suction channel that is configured to extend through at least a portion of cross-section of the handle and the blade;
        at least one sensor that is located between the proximal portion and the distal tip of the blade and further configured to detect raw data once intubated in a patient;
        an electronic component module that is configured to convert the raw data into the at least one output signal;
        a sensor tube cavity within the handle and the blade that is configured to extend from the electronic component module to the at least one sensor; and
        a flexible sensor tube that is configured to connect the electronic component module to the at least one sensor in order to transmit data from the at least one sensor to the electronic component module,
        wherein the flexible sensor tube passes through the sensor tube cavity within the handle and the blade,
        wherein the blade is configured to protrude outwardly at a substantially perpendicular angle from the handle to the distal tip,
        wherein the blade further comprises:
            (a) at least one inlet near the distal tip; and
            (b) at least one inlet between the distal tip and the proximal portion,
        wherein the handle is sized and shaped to be coupled to the electronic component module,
        wherein the electronic component module comprises integrated circuitry, and
        wherein the at least one outlet, the at least one inlet near the distal tip, the at least one inlet between the distal tip and the proximal portion, and the at least one suction channel, are configured to be in fluid communication with each other.

53. The system of claim 52, wherein the system further comprises a hosted server that is (i) configured to store and analyze the at least one output signal and (ii) connected to a local device and the computing device via the communications network.

54. The system of claim 53, wherein the hosted server is further configured to (i) determine a current anatomical location of the laryngoscope inside a patient; (ii) determine a route to a preferred anatomical location inside the patient; and (iii) provide a digital guidance for a user to follow so that the user can guide the laryngoscope to the preferred anatomical location.

55. The system of claim 54, wherein the current anatomical location, the preferred anatomical location, the route to the preferred anatomical location, and the digital guidance are determined by at least one selected from the group of: a probability algorithm, and a machine learning algorithm.

56. The system of claim 55, wherein the probability algorithm or the machine learning algorithm is stored inside the computing device.

57. The system of claim 55, wherein the probability algorithm or the machine learning algorithm is stored inside the laryngoscope.

58. The system of claim 52, wherein the integrated circuitry provides at least one functionality of: pH sensing, CO2 sensing, acoustic sensing, capacitance sensing, inductance sensing, temperature sensing, specific molecule sensing, binocular image sensing, monocular image sensing, arrayed image sensing, ambient color sensing, USB video device class (UVC), generating light and measuring a frequency of light that is reflected by its surroundings, or any combination thereof.

59. A laryngoscope comprising;
    a handle comprising a top portion, a bottom portion, and at least one outlet;
    a blade with a distal tip and a proximal portion wherein the proximal portion is connected to the bottom portion of the handle;
    at least one fluid channel that is configured to extend through at least a portion of cross-section of the handle and the blade;
    at least one sensor that is located between the proximal portion and the distal tip of the blade and further configured to detect raw data once intubated in a patient;
    an electronic component module;
    a sensor tube cavity within the handle and the blade that is configured to extend from the electronic component module to the at least one sensor;
    a flexible sensor tube that is configured to connect the electronic component module to the at least one sensor in order to transmit data from the at least one sensor to the electronic component module, wherein the flexible sensor tube passes through the sensor tube cavity within the handle and the blade; and a network radio configured to (i) transmit the detected raw data and (ii) receive instructions from a user with regards to use of the laryngoscope based at least in part on the detected raw data, wherein the blade is configured to protrude outwardly at a substantially perpendicular angle from the handle to the distal tip, wherein the blade further comprises:
  (a) at least one inlet near the distal tip; and
  (b) at least one inlet between the distal tip and the proximal portion, wherein the handle is sized and shaped to be coupled to the electronic component module, wherein the electronic component module comprises at least one integrated circuitry, and wherein the at least one outlet, the at least one inlet near the distal tip, the at least one inlet between the distal tip and the proximal portion, and the at least one fluid channel, are configured to be in fluid communication with each other.

60. The laryngoscope of claim 59, wherein the at least one integrated circuitry provides at least one functionality of: pH sensing, CO2 sensing, acoustic sensing, capacitance sensing, inductance sensing, temperature sensing, specific molecule sensing, binocular image sensing, monocular image sensing, arrayed image sensing, ambient color sensing, USB video device class (UVC), generating light and measuring a frequency of light that is reflected by its surroundings, or any combination thereof.

61. A computer readable storage medium tangibly embodying a computer readable program code having computer readable instructions which, when implemented, cause a computer to carry out the steps of:

detecting at least one anatomical feature of a patient by at least one sensor on a laryngoscope once the laryngoscope is intubated into the patient by a user, the at least one sensor including an image sensor and an inductive sensor;

transmitting the at least one anatomical feature to an electronic component module;

determining a preferred route of the laryngoscope inside the patient by the electronic component module;

sending the preferred route to a remote device to be displayed as an anatomical overlay on a graphic user interface; and providing the laryngoscope to the preferred route inside the patient via the anatomical overlay.

62. The computer readable storage medium of claim 61, wherein the at least one anatomical feature comprises at least one of: pH, $CO_2$, acoustic, capacitance, inductance, temperature, specific molecule, binocular image, monocular image, arrayed image, and ambient color.

* * * * *